(12) United States Patent
Murdoch et al.

(10) Patent No.: US 9,446,159 B2
(45) Date of Patent: Sep. 20, 2016

(54) FLOW CYTOMETER BIOSAFETY HOOD AND SYSTEMS INCLUDING THE SAME

(71) Applicant: Becton, Dickinson and Company, Franklin Lakes, NJ (US)

(72) Inventors: Steven Murdoch, San Ramon, CA (US); Scott Horton, San Jose, CA (US); Gil Reinin, Mountain View, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 14/505,028

(22) Filed: Oct. 2, 2014

(65) Prior Publication Data

US 2015/0099262 A1 Apr. 9, 2015

Related U.S. Application Data

(60) Provisional application No. 61/886,551, filed on Oct. 3, 2013.

(51) Int. Cl.
*A61L 2/20* (2006.01)
*B01L 1/02* (2006.01)
*G01N 15/14* (2006.01)
(Continued)

(52) U.S. Cl.
CPC .. *A61L 2/20* (2013.01); *B01L 1/02* (2013.01); *G01N 15/1459* (2013.01); *B01L 2200/082* (2013.01); *B01L 2300/0681* (2013.01);
(Continued)

(58) Field of Classification Search
CPC ............ A61L 2/20; A61L 2/022; B01L 1/02; G01N 15/1459
See application file for complete search history.

(56) References Cited

U.S. PATENT DOCUMENTS 5,441,708 A 8/1995 Diccianni et al.
5,641,457 A 6/1997 Vardanega et al.
(Continued)

FOREIGN PATENT DOCUMENTS

WO 01/85088 A1 11/2001

OTHER PUBLICATIONS

BD Biosciences, BD FACSDiva Software Quick Refernce Guide for BD FASCAria Cell Sorters, Jan. 2009, 8 pages, Available onlilne: http://www.bdbiosciences.com/documents/facsdivav61_aria_quickrefguide.pdf.
(Continued)

*Primary Examiner* — Regina M Yoo
(74) *Attorney, Agent, or Firm* — Kyle A. Gurley; Bret E. Field; Bozicevic, Field & Francis LLP

(57) ABSTRACT

Flow cytometer systems are provided that mitigate aerosols generated during operation of a flow cytometer. A flow cytometer system can include various combinations of: a flow cytometer instrument base, a flow cytometer, and a biosafety hood (BSH). In some embodiments, a subject flow cytometer system includes a flow cytometer instrument base, a flow cytometer, and a BSH. In some embodiments, a subject flow cytometer system includes a flow cytometer instrument base and a flow cytometer. In some cases, a BSH includes an aerosol management system, which provides a redundant air filtration system. Also provided are components of a flow cytometer system (e.g., a BSH configured to attach to a flow cytometer instrument base, a flow cytometer instrument base configured to attach to a BSH, etc.). Also provided are methods, including methods of performing a flow cytometric procedure using a flow cytometer system; and methods of decontaminating a flow cytometer system.

21 Claims, 6 Drawing Sheets

(51) Int. Cl.
    *G01N 15/10* (2006.01)
    *G01N 35/00* (2006.01)
(52) U.S. Cl.
    CPC ............... *G01N2015/1006* (2013.01); *G01N 2035/00306* (2013.01)

(56) References Cited

U.S. PATENT DOCUMENTS

| | | | |
|---|---|---|---|
| 5,700,692 | A | 12/1997 | Sweet |
| 5,776,781 | A | 7/1998 | Vardanega et al. |
| 6,014,904 | A | 1/2000 | Lock |
| 6,372,506 | B1 | 4/2002 | Norton |
| 6,510,007 | B1 | 1/2003 | Blasenheim |
| 6,683,314 | B2 | 1/2004 | Oostman, Jr. et al. |
| 6,809,804 | B1 | 10/2004 | Yount et al. |
| 6,880,414 | B2 | 4/2005 | Norton |
| 6,936,434 | B2 * | 8/2005 | McDonnell ............ A61L 2/208 422/26 |
| 6,944,338 | B2 | 9/2005 | Lock et al. |
| 7,129,505 | B2 | 10/2006 | Oostman, Jr. et al. |
| 7,201,875 | B2 | 4/2007 | Norton et al. |
| 7,544,326 | B2 | 6/2009 | Norton et al. |
| 2002/0042148 | A1 | 4/2002 | Monard |
| 2003/0071543 | A1 * | 4/2003 | Daghighian ............ B25J 21/02 312/1 |
| 2009/0127167 | A1 * | 5/2009 | Kirstein ............ G01N 15/1459 209/44.1 |
| 2014/0170697 | A1 * | 6/2014 | Sharpe ............ G01N 15/1436 435/30 |

OTHER PUBLICATIONS

BD Biosciences, BD FACSAria III User's Guide, May 2012, 346 pages, Available online: http://www.bdbiosciences.com/documents/BD_FACSAria_III_User_Guide.pdf.

BD Biosciences, BD FACSAria III Cell Sorter: Technical Specifications, 2010, 4 pages, Available online: http://www.bdbiosciences.com/documents/BD_FACSAria_III_tech_specs.pdf.

BD Biosciences, BD FACSAria III Cell Sorter Brochure, 2010, 16 pages, Available online: http://www.bdbiosciences.com/documents/BD_FACSAria_III_brochure.pdf.

BD Biosciences, BD FACSAria Fusion Cell Sorter: Technical Specificaitons, 23-15075-02, label approval notification Jul. 16, 2014, available in print Aug. 11, 2014, 4 pages, Available online: http://www.bdbiosciences.com/documents/BD_FACSAria_fusion_tech_specs.pdf.

BD Biosciences, BD FACSAria Fusion Cell Sorter: Recommended Filter Guide, 23-15074-0, label approval notification Sep. 25, 2014, available in print Oct. 6, 2014, 1 page, Available online: http://www.bdbiosciences.com/docments/BD_FACSAria_fusion_filter_guide.pdf.

BD Biosciences, BD FACSAria Fusion Brochure, 23-14994-0, label approval notification Aug. 7, 2014, available in print Sep. 4, 2014, 20 pages, Available online: http://www.bdbiosciences.com/documents/BD_FACSAria_fusion_brochure.pdf.

* cited by examiner

FLOW CYTOMETER BIOSAFETY HOOD AND SYSTEMS INCLUDING THE SAME

CROSS-REFERENCE TO RELATED APPLICATIONS

Pursuant to 35 U.S.C. §119 (e), this application claims priority to the filing date of U.S. Provisional Patent Application Ser. No. 61/886,551 filed on Oct. 3, 2013; the disclosure of which application is herein incorporated by reference.

INTRODUCTION

Flow cytometers are valuable laboratory instruments for the analysis and isolation of biological particles, such as cells and constituent molecules. Flow cytometers utilize a fluid stream to linearly segregate particles such that they can pass, single file, through a detection apparatus measuring properties such as light scattering and/or fluorescence. Individual cells can then be characterized according to the measured properties (light scattering, the presence of detectable markers, etc.). Thus, flow cytometers can be used, for example, to produce a profile (e.g., a diagnostic profile) of a population of biological particles. Some flow cytometers can be used to sort the biological particles based on their measured properties.

SUMMARY

Flow cytometric analysis of a biological sample generates aerosols, and there is a need to provide biosafety containment of flow cytometer instruments (e.g., cell sorters) that are used to process hazardous substances such as hazardous chemicals and/or toxic or infectious particles. Flow cytometer systems are provided that mitigate aerosols generated during operation of a flow cytometer. In some embodiments, a flow cytometer system includes a biosafety hood designed to enclose an integrated flow cytometer. A flow cytometer system can include various combinations of: a flow cytometer instrument base, a flow cytometer, and a biosafety hood (BSH). In some embodiments, a subject flow cytometer system includes a flow cytometer instrument base, a flow cytometer, and a BSH. In some embodiments, a subject flow cytometer system includes a flow cytometer instrument base and a flow cytometer. In some cases, a BSH includes an aerosol management system, which provides a redundant air filtration system. Also provided are components of a flow cytometer system (e.g., a BSH configured to attach to a flow cytometer instrument base, a flow cytometer instrument base configured to attach to a BSH, etc.). Also provided are methods, including methods of performing a flow cytometric procedure using a flow cytometer system; and methods of decontaminating a flow cytometer system.

BRIEF DESCRIPTION OF THE FIGURES

FIG. 3 panel A depicts a step of introducing a sample into a sample loading region 310 of a flow cytometer 300 of a subject flow cytometer system that includes a flow cytometer instrument base 100, and biosafety hood (BSH) 200. FIG. 3 panel B depicts an operator (i.e., a user) manipulating a sample within a particle collection region 330 of a flow cytometer 300, where the flow cytometer system includes a BSH. FIG. 3 panel C depicts a flow cytometer instrument base 100 that houses spectral filters and detector arrays of an associated flow cytometer. FIG. 3 panel D depicts a flow cytometer instrument base 100 having multiple removable fluid sources in a drawer that is extendible from the base.

DETAILED DESCRIPTION

Figure 1:
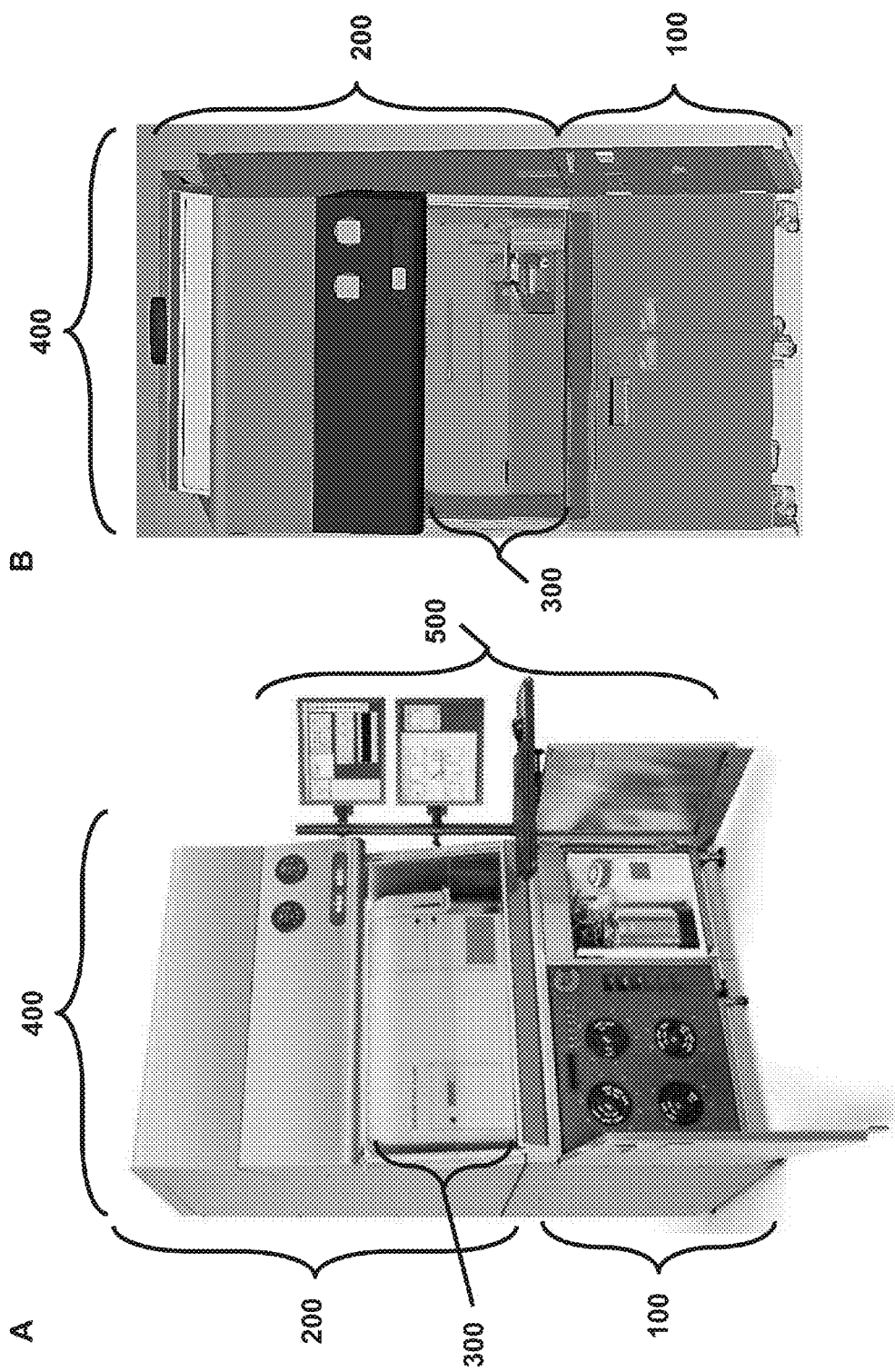
FIG. 1 panels A-B depict one embodiment of a flow cytometer system 400 that includes a flow cytometer instrument base 100, a biosafety hood (BSH) 200, and a flow cytometer 300.

Flow cytometer systems are provided that mitigate aerosols generated during operation of a flow cytometer. A flow cytometer system can include various combinations of: a flow cytometer instrument base, a flow cytometer, and a biosafety hood (BSH). In some embodiments, a subject flow cytometer system includes a flow cytometer instrument base, a flow cytometer, and a BSH. In some embodiments, a subject flow cytometer system includes a flow cytometer instrument base and a flow cytometer. In some cases, a BSH includes an aerosol management system, which provides a redundant air filtration system. Also provided are components of a flow cytometer system (e.g., a BSH configured to attach to a flow cytometer instrument base, a flow cytometer instrument base configured to attach to a BSH, etc.). Also provided are methods, including methods of performing a flow cytometric procedure using a flow cytometer system; and methods of decontaminating a flow cytometer system.

Before embodiments of the present disclosure are described in greater detail, it is to be understood that this disclosure is not limited to particular embodiments described, as such may, of course, vary. The disclosure encompasses various alternatives, modifications, and equivalents, as will be appreciated by those of skill in the art. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

In determining whether a number is near to or approximately a specifically recited number, the near or approximating unrecited number may be a number which, in the context in which it is presented, provides the substantial equivalent of the specifically recited number.

It is noted that, as used herein and in the appended claims, the singular forms "a", "an", and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which can be readily separated from or combined with the features of any of the other several embodiments without departing from the scope or spirit of the present disclosure. Any recited method can be carried out in the order of events recited or in any other order which is logically possible.

Any publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided may be different from the actual publication dates which may need to be independently confirmed.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, representative illustrative methods and materials are now described.

In further describing embodiments of the present disclosure, aspects of embodiments of the flow cytometer systems will be described in greater detail. Methods of using the subject flow cytometer systems will then be reviewed.

Flow Cytometer System

Aspects of the disclosure include a flow cytometer system. A flow cytometer system can include various combinations of the following components: a flow cytometer instrument base, a flow cytometer, and a biosafety hood (BSH). In some embodiments, a subject flow cytometer system includes a flow cytometer instrument base, a flow cytometer, and a BSH (FIG. 1). In some embodiments, a subject flow cytometer system includes a flow cytometer instrument base and a flow cytometer (FIG. 2), which components may be integrated. In some embodiments, a subject flow cytometer system includes a flow cytometer instrument base and a BSH, where the base does not include any flow cytometer components but is configured to receive a separate flow cytometer, e.g., a desk top cytometer. In some cases, a BSH includes an aerosol management system (AMS) operatively coupled to the flow cytometer. Aspects of the disclosure also include the individual components of a flow cytometer system (e.g., a BSH configured to attach to a flow cytometer instrument base, a flow cytometer instrument base configured to attach to a BSH, etc.). The components, which will now be described in greater detail below, can be made of any convenient durable, rigid material, or combination of materials, including but not limited to: metal (e.g., stainless steel); plastic (e.g., polycarbonate, LEXAN, etc.); and the like.

Biosafety Hood (BSH)

In some embodiments, the present disclosure provides a biosafety hood (BSH). The term "hood" is used herein to refer to an enclosure or canopy provided with a draft (i.e., air flow) for carrying off aerosols, fumes, sprays, smokes, or dusts. A "biosafety hood" is therefore a hood intended to facilitate the safe handling of biologically related materials (e.g., aerosols containing dangerous, toxic, and/or infectious particles, etc.). In some instances, the BSH is configured to keep aerosols from escaping. In some instances, the BSH is configured to maintain purity of the materials being analyzed/sorted by the flow cytometer. As such, in some instances the BSH is configured to keep both particles from escaping the interior of the BSH as well as entering the interior of the BSH.

A subject BSH is designed to form an enclosure (referred to herein as the "main enclosure") that can enclose a flow cytometer. The exact dimensions and shape of the BSH (and the main enclosure) therefore depend on the dimensions and shape of the flow cytometer to be enclosed. The BSH (and the main enclosure) can be of any convenient shape (e.g., dome-like, sphere-like, cube-like, cuboid-like, cylinder-like, pyramid-like, cone-like, hexagonal prism-like, triangular prism-like, etc.). As described below, a BSH can include all sides/surfaces of its shape, or a BSH can be missing one or more sides or surfaces.

In some embodiments, the BSH can have greater overall dimensions than the main enclosure (described below) that the BSH defines. For example, the BSH can include an additional compartment, separate from (and not enclosed by) the main enclosure. In some cases, a BSH has a region (e.g., an upper region) that can house any convenient component, e.g., an air filtration system, a fan, a blower assembly, ducting, hoses, conduits, a processor, an aerosol management system (AMS), etc. In some such cases, therefore, the dimensions (e.g., height, width, and/or depth) of the BSH are greater than the dimensions of the main enclosure that the BSH defines.

In some embodiments, the height of the BSH is in a range of from 2 feet (ft) to 10 feet (ft) (e.g., from 2 ft to 9 ft, from 2 ft to 8 ft, from 2 ft to 7 ft, from 2 ft to 6 ft, from 2 ft to 5 ft, from 2 ft to 4 ft, from 2 ft to 3 ft, from 3 ft to 5 ft, from 3.5 ft to 5.5 ft, from 3 ft to 4 ft, 2 ft, 3 ft, 4 ft, 5 ft, 6 ft, 7 ft, 8 ft, 9 ft, or 10 ft, etc.). Because the BSH can enclose a flow cytometer, the height of the BSH is greater than the height of the flow cytometer to be enclosed. In some cases, the height of the BSH is in a range of from 100.05% to 250% the height of the flow cytometer to be enclosed (e.g., from 100.05% to 225%, from 100.05% to 200%, from 100.05% to 175%, from 100.05% to 170%, from 100.05% to 165%, from 100.05% to 160%, from 100.05% to 150%, from 100.05% to 140%, from 100.05% to 130%, from 100.05% to 125%, from 100.05% to 120%, from 100.05% to 115%, from 100.05% to 110%, from 100.05% to 107.5%, from 100.05% to 105%, or from 100.05% to 102.5%).

In some cases, the width of the BSH is in a range of from 2 feet (ft) to 10 feet (ft) (e.g., from 2 ft to 9 ft, from 2 ft to 8 ft, from 2 ft to 7 ft, from 2 ft to 6 ft, from 2 ft to 5 ft, from 2 ft to 4 ft, from 2 ft to 3 ft, from 3 ft to 5 ft, from 3.5 ft to 5.5 ft, from 3 ft to 4 ft, 2 ft, 3 ft, 4 ft, 5 ft, 6 ft, 7 ft, 8 ft, 9 ft, or 10 ft, etc.). Because the BSH can enclose a flow cytometer, the width of the BSH is greater than the width of the flow cytometer to be enclosed. In some cases, the width of the BSH is in a range of from 100.05% to 250% the width of the flow cytometer to be enclosed (e.g., from 100.05% to 225%, from 100.05% to 200%, from 100.05% to 175%, from 100.05% to 170%, from 100.05% to 165%, from 100.05% to 160%, from 100.05% to 150%, from 100.05% to 140%, from 100.05% to 130%, from 100.05% to 125%, from 100.05% to 120%, from 100.05% to 115%, from 100.05% to 110%, from 100.05% to 107.5%, from 100.05% to 105%, or from 100.05% to 102.5%).

In some cases, the depth of the BSH is in a range of from 2 feet (ft) to 10 feet (ft) (e.g., from 2 ft to 9 ft, from 2 ft to 8 ft, from 2 ft to 7 ft, from 2 ft to 6 ft, from 2 ft to 5 ft, from 2 ft to 4 ft, from 2 ft to 3 ft, from 3 ft to 5 ft, from 3.5 ft to 5.5 ft, from 3 ft to 4 ft, 2 ft, 3 ft, 4 ft, 5 ft, 6 ft, 7 ft, 8 ft, 9 ft, or 10 ft, etc.). Because the BSH can enclose a flow cytometer, the depth of the BSH is greater than the depth of the flow cytometer to be enclosed. In some cases, the depth of the BSH is in a range of from 100.05% to 250% the depth of the flow cytometer to be enclosed (e.g., from 100.05% to 225%, from 100.05% to 200%, from 100.05% to 175%, from 100.05% to 170%, from 100.05% to 165%, from 100.05% to 160%, from 100.05% to 150%, from 100.05% to 140%, from 100.05% to 130%, from 100.05% to 125%, from 100.05% to 122.5%, from 100.05% to 120%, from 100.05% to 115%, from 100.05% to 110%, from 100.05% to 107.5%, from 100.05% to 105%, or from 100.05% to 102.5%).

Enclosure.

A suitable BSH can attach to a flow cytometer instrument base (described in more detail below) such that an enclosure exists (the 'main enclosure') that is large enough to contain a flow cytometer. Thus, in some cases, an instrument base is configured to attach to a BSH, and/or a BSH is configured to attach to an instrument base. By "configured to attach" is meant that a component is designed in such a way as to facilitate attachment to another component. For example, in some cases, "configured to attach" can mean that at least a portion of a surface of a first component is flat, thus allowing adhesion to the surface of a second component. As another example, in some cases, "configured to attach" can mean that a first component can have holes, tabs, ridges, slots, etc. to allow the first component to attach to a second component. How a particular component is "configured to attach" to another component can depend, for example, on how the two components are to be attached (e.g., screws, bolts, clips, adhesive, sealant, etc.).

The exact dimensions (and shape) of the main enclosure will depend on the dimensions and shape of the flow cytometer to be enclosed. However, because the main enclosure is designed to contain a flow cytometer, the volume of the main enclosure is equal to or greater than the volume to be occupied by the flow cytometer. In order to reduce the overall footprint of a subject flow cytometer system, the volume of the main enclosure is designed to be small relative to the volume occupied by the flow cytometer to be enclosed.

In some embodiments, the volume of the main enclosure (i.e., the volume enclosed) is in a range of from 15 cubic feet (cf) to 60 cf (e.g., 15 cf to 50 cf, 15 cf to 40 cf, 15 cf to 35 cf, 15 cf to 30 cf, 17.5 cf to 35 cf, 17.5 cf to 30 cf, 17.5 cf to 27.5 cf, 17.5 cf to 25 cf, 17.5 cf to 22.5 cf, 20 cf to 25 cf, 20 cf to 22.5 cf, 21 cf to 22 cf, or 22 cf to 25 cf). In some cases, the volume of the main enclosure is in a range of from 100.05% to 200% the volume occupied by the flow cytometer to be enclosed (e.g., from 100.05% to 190%, from 100.05% to 180%, from 100.05% to 170%, from 100.05% to 160%, from 100.05% to 150%, from 100.05% to 145%, from 100.05% to 140%, from 100.05% to 135%, from 100.05% to 130%, from 100.05% to 125%, from 100.05% to 120%, from 100.05% to 115%, from 100.05% to 110%, from 100.05% to 107.5%, from 100.05% to 105%, or from 100.05% to 102.5%).

In some embodiments, the height of the main enclosure is in a range of from 2 feet (ft) to 10 feet (ft) (e.g., from 2 ft to 9 ft, from 2 ft to 8 ft, from 2 ft to 7 ft, from 2 ft to 6 ft, from 2 ft to 5 ft, from 2 ft to 4 ft, from 2 ft to 3 ft, from 3 ft to 5 ft, from 3.5 ft to 5.5 ft, from 3 ft to 4 ft, 2 ft, 3 ft, 4 ft, 5 ft, 6 ft, 7 ft, 8 ft, 9 ft, or 10 ft, etc.). Because the main enclosure is designed to contain a flow cytometer, the height of the main enclosure is equal to or greater than the height of the flow cytometer to be enclosed. In some cases, the height of the main enclosure is in a range of from 100.05% to 250% the height of the flow cytometer to be enclosed (e.g., from 100.05% to 225%, from 100.05% to 200%, from 100.05% to 175%, from 100.05% to 170%, from 100.05% to 165%, from 100.05% to 160%, from 100.05% to 150%, from 100.05% to 140%, from 100.05% to 130%, from 100.05% to 125%, from 100.05% to 120%, from 100.05% to 115%, from 100.05% to 110%, from 100.05% to 107.5%, from 100.05% to 105%, or from 100.05% to 102.5%).

In some cases, the width of the main enclosure is in a range of from 2 feet (ft) to 10 feet (ft) (e.g., from 2 ft to 9 ft, from 2 ft to 8 ft, from 2 ft to 7 ft, from 2 ft to 6 ft, from 2 ft to 5 ft, from 2 ft to 4 ft, from 2 ft to 3 ft, from 3 ft to 5 ft, from 3.5 ft to 5.5 ft, from 3 ft to 4 ft, 2 ft, 3 ft, 4 ft, 5 ft, 6 ft, 7 ft, 8 ft, 9 ft, or 10 ft, etc.). Because the main enclosure is designed to contain a flow cytometer, the width of the main enclosure is equal to or greater than the width of the flow cytometer to be enclosed. In some cases, the width of the main enclosure is in a range of from 100.05% to 250% the width of the flow cytometer to be enclosed (e.g., from 100.05% to 225%, from 100.05% to 200%, from 100.05% to 175%, from 100.05% to 170%, from 100.05% to 165%, from 100.05% to 160%, from 100.05% to 150%, from 100.05% to 140%, from 100.05% to 130%, from 100.05% to 125%, from 100.05% to 120%, from 100.05% to 115%, from 100.05% to 110%, from 100.05% to 107.5%, from 100.05% to 105%, or from 100.05% to 102.5%).

In some cases, the depth of the main enclosure is in a range of from 2 feet (ft) to 10 feet (ft) (e.g., from 2 ft to 9 ft, from 2 ft to 8 ft, from 2 ft to 7 ft, from 2 ft to 6 ft, from 2 ft to 5 ft, from 2 ft to 4 ft, from 2 ft to 3 ft, from 3 ft to 5 ft, from 3.5 ft to 5.5 ft, from 3 ft to 4 ft, 2 ft, 3 ft, 4 ft, 5 ft, 6 ft, 7 ft, 8 ft, 9 ft, or 10 ft, etc.). Because the main enclosure is designed to contain a flow cytometer, the depth of the main enclosure is equal to or greater than the depth of the flow cytometer to be enclosed. In some cases, the depth of the main enclosure is in a range of from 100.05% to 250% the depth of the flow cytometer to be enclosed (e.g., from 100.05% to 225%, from 100.05% to 200%, from 100.05% to 175%, from 100.05% to 170%, from 100.05% to 165%, from 100.05% to 160%, from 100.05% to 150%, from 100.05% to 140%, from 100.05% to 130%, from 100.05% to 125%, from 100.05% to 122.5%, from 100.05% to 120%, from 100.05% to 115%, from 100.05% to 110%, from 100.05% to 107.5%, from 100.05% to 105%, or from 100.05% to 102.5%).

In some embodiments, the main enclosure is defined by a combination of surfaces of the BSH and the instrument base. Thus, in such cases, the BSH does not include all of the surfaces that define the main enclosure. For example, the BSH may not include one or more of: a bottom surface (i.e., a floor), a back surface, and/or a side surface, such that the missing surface(s) can be provided by the instrument base. For example, in some cases, the BSH does not include a floor, and the bottom surface of the main enclosure is therefore defined by an upward-facing surface of the instrument base. In some cases, the BSH has a bottom surface such that the bottom surface of the main enclosure is defined by the bottom surface of the BSH. In some such cases, the bottom surface of the BSH attaches to a surface (e.g., an upward facing surface) of the instrument base. In some cases, all surfaces of the main enclosure are defined by the BSH. For example, in some cases, a subject BSH includes a floor, a ceiling, and all sides (e.g., a front, a back, and sides).

Any convenient type of attachment (e.g., bolts, clamps, pegs, latches, screws, magnets, adhesives, sealants and the like) can be used to attach an instrument base to a BSH. In some cases (e.g., in embodiments where at least one surface of the main enclosure is defined by the instrument base), the BSH and the instrument base are attached such that they form a seal to prevent aerosols from escaping the main enclosure at the site(s) of attachment. Any convenient method/substance can be used to form a seal. In some cases, a gasket (e.g., a rubber gasket) is used. In some cases, a sealant is used. Any of a wide variety of sealants can be used, and the selection of a sealant will generally depend on the material makeup of the BSH and the instrument base, as well as the type of aerosols and/or gases (e.g., decontamination gas) to which the sealant may be exposed. Examples of suitable sealants include, but are not limited to: silicon sealants, acrylic sealants, adhesive sealants, epoxy sealants, foam sealants, gasket sealants, glass sealants, impregnating sealants, latex sealants, metal sealants, plastic sealants, polysulfide sealants, polyurethane sealants, rubber sealants, seam sealants, urethane sealants, etc.

In some embodiments, a flow cytometer has non-aerosol generating components that are not part of the sample flow path and are not contained by the main enclosure of the BSH. For example, components such as spectral filters, lasers, detector arrays, etc. can be housed outside of the main enclosure of the BSH. For example, in some embodiments, a flow cytometer instrument base contains non-aerosol generating components of an associated flow cytometer (FIG. 3C). Thus, for example, the phrase "the flow cytometer is present in an enclosure defined by the BSH and the flow cytometer instrument base" does not mean that all components of the flow cytometer are necessarily contained within the main enclosure. Instead, such a phrase means that at least the flow path (i.e., the potential aerosol generating components: the sample loading region, the particle interrogation region, and the particle collection region) of the flow cytometer is present in the main enclosure.

Air Filtration System(s).

A subject BSH has at least one air filtration system, referred to herein as a "main" air filtration system or a "first" air filtration system. An air filtration system is used to remove hazardous materials (e.g., infectious particles and/or toxins, hazardous chemicals, etc.) via air flow. The main (first) air filtration system of a BSH removes aerosols from the main enclosure.

An air filtration system includes a blower to generate air flow. The term "blower" or "blower assembly" is used herein to refer to any type of device that can be used to generate air flow (e.g., using a fan mechanism, using a turbine-based mechanism, using a bellows-based mechanism, etc.). Any convenient type of blower may be used that generates an appropriate amount of air flow as desired. In some embodiments, a blower includes a fan. In some embodiments, the speed of air flow generated by the blower can be controlled by a user (e.g., via an instrument control panel associated with the BSH, via a processor that can control the blower, etc.).

In some embodiments, the blower of any one or more air filtration systems (e.g., the main blower, i.e., the blower of the main air filtration system; the AMS blower, i.e., the blower an aerosol management system; etc.) can operate at two or more speed settings (e.g., low (LO), medium (MED), and/or high (HI)). Speed settings can be set for any convenient speed (e.g., 5 cubic feet per minute (cfm), 10 cfm, 15 cfm, 20 cfm, 25 cfm, 30 cfm, 35 cfm, 40 cfm, 45 cfm, 50 cfm, 55 cfm, 60 cfm, 65 cfm, 70 cfm, 75 cfm, 80 cfm, 85 cfm, 90 cfm, 95 cfm, 100 cfm, 105 cfm, 110 cfm, 115 cfm, 120 cfm, 125 cfm, 130 cfm, 135 cfm, 140 cfm, 145 cfm, 150 cfm, 155 cfm, 160 cfm, 165 cfm, etc.). In some cases, a blower can be controlled by a variable speed setting. For example, in some cases, speed settings can range from 5 cubic feet per minute (cfm) to 300 cfm (from 10 cfm to 200 cfm, from 10 cfm to 150 cfm, from 10 cfm to 100 cfm, from 10 cfm to 80 cfm, from 10 cfm to 60 cfm, from 10 cfm to 50 cfm, from 10 cfm to 40 cfm, or from 15 cfm to 40 cfm).

In some embodiments, an air filtration system has an air filter (to filter particles from the air). Any convenient air filter may be used. The choice of filter will depend on various factors that may include desired level of filtration, ease of maintenance, cost, etc. Examples of suitable filters include, but are not limited to: high efficiency particulate air (HEPA) filters (also sometimes referred to as high efficiency particulate arrestance filters, high efficiency particulate absorbing filters, etc.), activated carbon air filters, polyester and pleated filters, fiberglass filters, ionic air filters (i.e., air ionizers), UV light air filters, and the like.

In some embodiments, the air filter is a HEPA filter, which is a filter designed to remove particulates, including microorganisms and infectious agents, from the air. HEPA filters are available from numerous commercial sources, are available in many different shapes and sizes, and can be designed to fit almost any device that utilizes air flow (e.g., vacuum cleaners, household air filters, automobiles, biomedical devices, etc.). To be classified as a HEPA filter, a filter must satisfy certain standards of efficiency such as those set by the United States Department of Energy (DOE). To qualify as HEPA, an air filter must remove (from the air that passes through) a minimal percent of particles that have a diameter of 0.3 µm. In some cases, medical-use HEPA filtration systems also incorporate high-energy ultra-violet light units to kill off the live bacteria and viruses trapped by the filter media. Some of the highest-rated HEPA units have an efficiency rating of 99.995%, which assures a very high level of protection against airborne disease transmission. Thus, in some embodiments, a subject HEPA filter is accompanied by a high-energy ultra-violet light unit that can be used to kill off trapped particles (e.g., bacteria, fungi, viruses, etc.). In some embodiments, a subject HEPA filter has an efficiency rating of 99.5% or more (e.g., 99.7% or more, 99.8% or more, 99.9% or more, 99.92% or more, 99.93% or more, 99.94% or more, 99.95% or more, 99.96% or more, 99.97% or more, 99.98% or more, 99.99% or more, 99.995% or more, 99.9995% or more, 99.99995% or more, or 99.999995% or more).

The air filter may be positioned anywhere along the path of air flow that is generated by the blower of the air filtration system (e.g., at the beginning, at the end, or anywhere between). In some cases, the air filter is positioned at a convenient location for removal, cleaning, and/or replacement by an operator (i.e., user). In some cases, an air filtration system does not have an air filter. In such cases, aerosols can be removed from the BSH by flowing them out of the BSH (e.g., using the air flow generated by the blower) without filtration.

Figure 4:
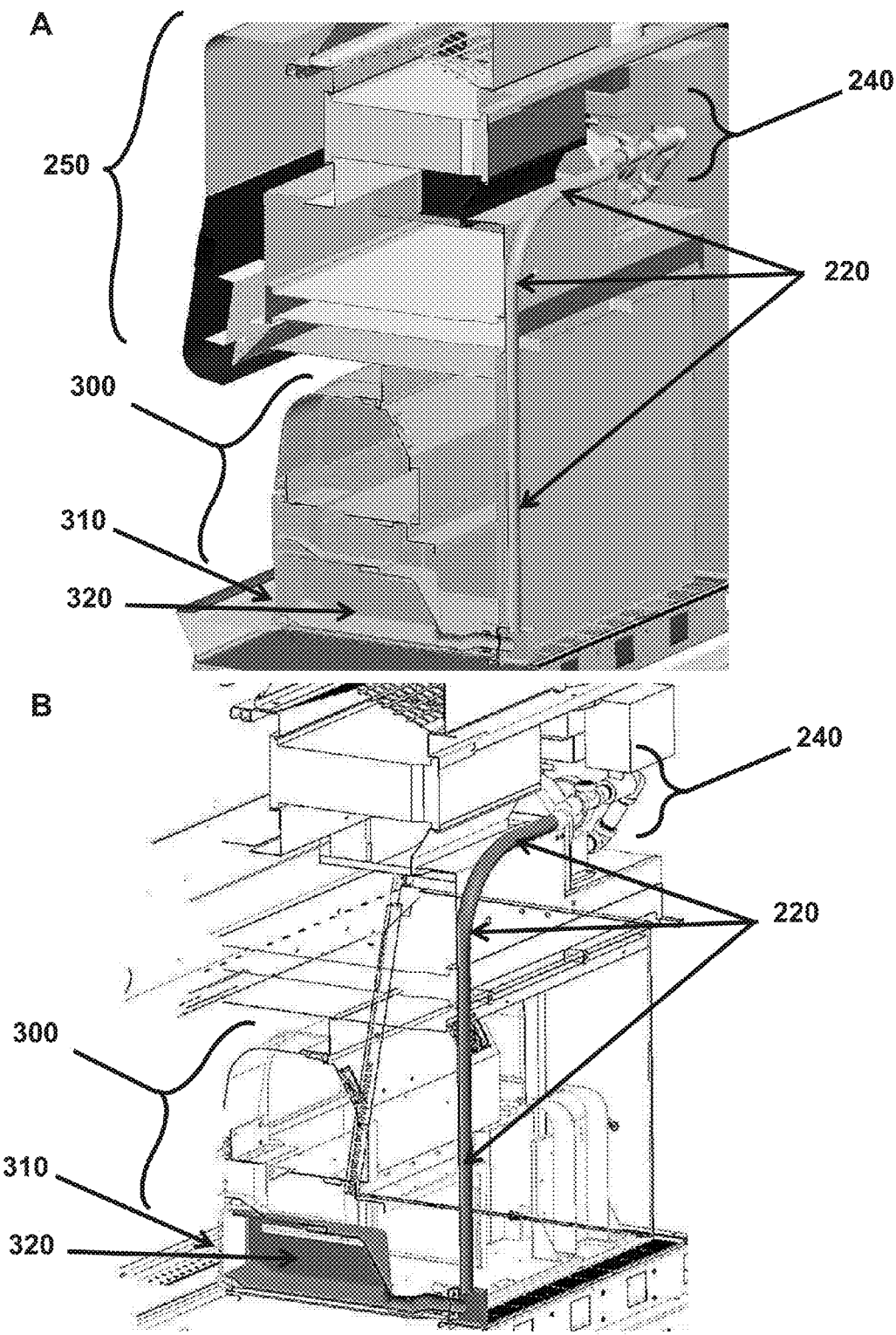
FIG. 4 panels A-B depict a cutaway schematic of one embodiment of a biosafety hood (BSH) having an aerosol management system (AMS) 240 that is fluidically coupled via conduit 220 to a sample manipulation chamber of the particle collection region 320 of a flow cytometer 300. The sample manipulation chamber of the particle collection region 320 has an opening for an air filter 310 facing toward the front of the flow cytometer 300. The BSH depicted has an upper region that houses first and a second air filtration systems 250.

A blower assembly and/or air filter can be positioned in a region (e.g., an upper region) of the BSH that is not encapsulated by the main enclosure (i.e., the enclosure that is present when the BSH and instrument base are attached). Such a region (e.g., an upper region) can house any convenient component, e.g., an air filtration system, a fan, a blower assembly, ducting, hoses, conduits, a processor, an aerosol management system (AMS), etc. (FIG. 4).

In some embodiments, the BSH includes an opening on one surface (e.g., a forward facing surface) that can be closed and/or sealed. For example, a BSH can have a movable panel (e.g., a sliding or hinged panel, referred to in the art as a "sash") that allows operator entry into the enclosure. The term "sash" (or "hood sash") refers to the movable front face of a subject BSH, usually in glass, usually capable of upward and downward movement (or side-to-side movement), often by virtue of a counterbalance mechanism. A sash acts as a physical barrier that helps to maintain a particulate-free environment and laminar air flow. A sash can be made of any convenient material, including a transparent or translucent material (e.g., glass, plastic, a durable thermoplastic, an impact and temperature resistant polymer such as LEXAN, and the like) to allow visualization of the contents of the enclosure when the sash is closed. In some cases, a movable panel (e.g., sash) can be closed and sealed Aerosol Management System (AMS).

In some embodiments, a BSH includes a first air filtration system and an Aerosol Management System (AMS). An AMS includes an air filtration system. Thus, a BSH having an AMS includes a first (main) air filtration system and a second (AMS) air filtration system.

While aerosols may be generated anywhere along the flow path of a flow cytometer, the majority of aerosols tend to be generated in the particle collection region. Thus, in some embodiments, an AMS can fluidically couple to the flow path, or to a region of the flow path, of a flow cytometer. In some embodiments, an AMS can fluidically couple (e.g., via a conduit, such as a hose, a tube, flexible ducting, etc.) to a particle collection region of a flow cytometer. The air filtration system of the AMS can therefore be referred to as being "dedicated" to the particle collection region with which it is coupled.

In some cases, the particle collection region includes a sample manipulation chamber. In general, a sample manipulation chamber is designed so that air flow through the chamber (e.g., via a fluidically coupled AMS) is streamlined so that aerosols can be removed from the chamber while at the same time reducing (e.g., minimizing) the chance of cross-contamination among samples within the chamber. A sample manipulation chamber is a chamber that encloses a region containing samples to be manipulated (e.g., to allow for the containment of generated aerosols). As such, in some cases, an AMS is fluidically coupled (e.g., via a conduit, such as a hose, a tube, flexible ducting, etc.) to a sample manipulation chamber.

In some embodiments, a sample manipulation chamber is an enclosed chamber (FIG. 3B, FIG. 4, FIG. 5, and FIG. 7), with exceptions that the sample manipulation chamber can include: (i) an opening (a filter port) for a filter on one side to allow clean air into the sample manipulation chamber; (ii) an opening (an AMS port) on one side that can fluidically couple to an AMS, e.g., the opening can be connected to a conduit (e.g., a hose, flexible tubing, flexible ducting, etc.) that can connect to an AMS (FIG. 4), which generates air flow; and (iii) an opening (a flow path port) to allow the flow path of the flow cytometer to enter the sample manipulation chamber.

Thus, a sample manipulation chamber does not have to be completely sealed. For example, in some cases, a sample manipulation chamber has an influx opening (e.g., a filter port) and/or an efflux opening (e.g., an AMS port) to allow fluid (e.g., air) to flow within the sample manipulation chamber. In some cases, a sample manipulation chamber has both an influx opening and an efflux opening. The size of an influx and/or efflux opening is only limited by the dimensions of the sample manipulation chamber. For example, an influx opening (e.g., a filter port) can simply be the absence of an entire face of the chamber (e.g., in influx opening of a sample manipulation chamber can be the entire front face)(e.g., see FIGS. 4-5 and 7). In some cases, an influx or eflux opening can be covered, e.g., by a filter (e.g., an air filter). In some cases, a sample manipulation chamber includes an influx opening (e.g., a filter port), an efflux opening (e.g., an AMS port), and an opening (a flow path port) to allow the flow path of the flow cytometer to enter the sample manipulation chamber.

In some cases, a sample manipulation chamber includes an air filter (described above). Any convenient air filter may be used. The choice of filter will depend on various factors that may include desired level of filtration, ease of maintenance, cost, etc. Examples of suitable filters include, but are not limited to: high efficiency particulate air (HEPA) filters (also sometimes referred to as high efficiency particulate arrestance filters, high efficiency particulate absorbing filters, etc.), activated carbon air filters, polyester and pleated filters, fiberglass filters, ionic air filters (i.e., air ionizers), UV light air filters, and the like.

Figure 5:
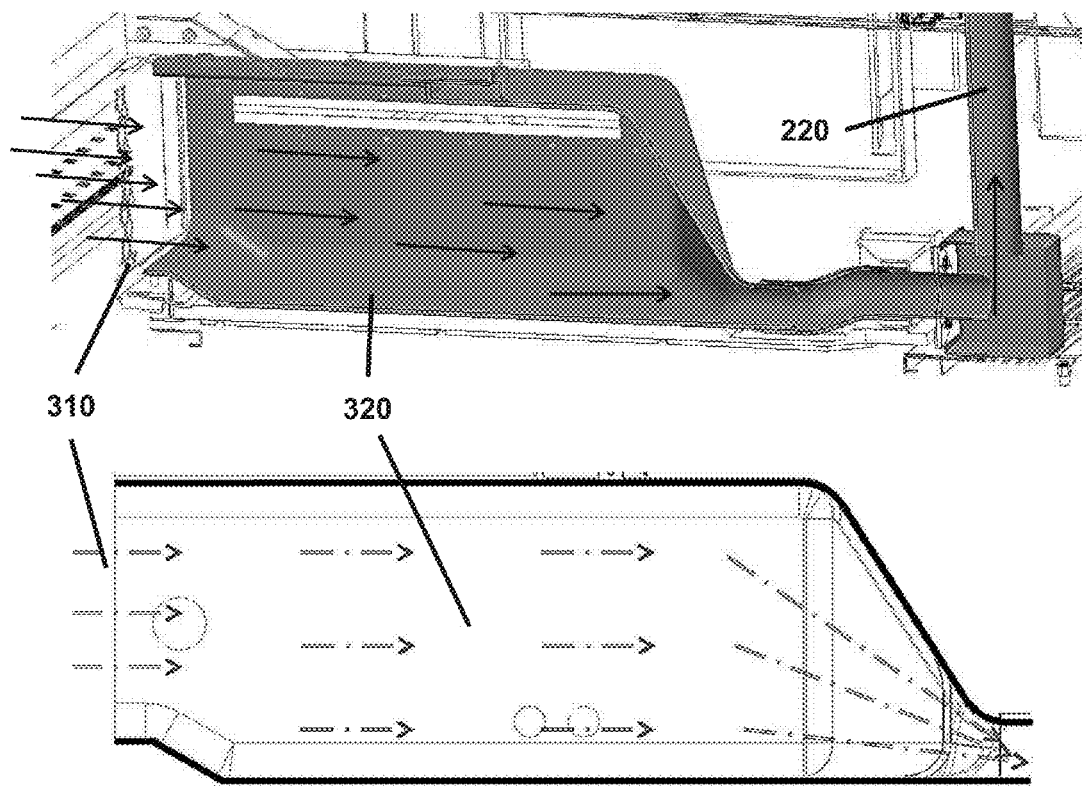
FIG. 5 depicts cutaway schematics of one embodiment of a flow cytometer system where a sample manipulation chamber of the particle collection region 320 of a flow cytometer is fluidically coupled via conduit 220 to an aerosol management system (AMS) of a biosafety hood (BSH). The sample manipulation chamber of the particle collection region 320 has an opening for an air filter 310 facing toward the front of the flow cytometer. When the AMS is operating, air flows (depicted with arrows) from the front of the flow cytometer, through forward-facing air filter 310 through the sample manipulation chamber of the particle collection region 320 toward the back of the flow cytometer, into the conduit 220 and toward the AMS.
Figure 7:
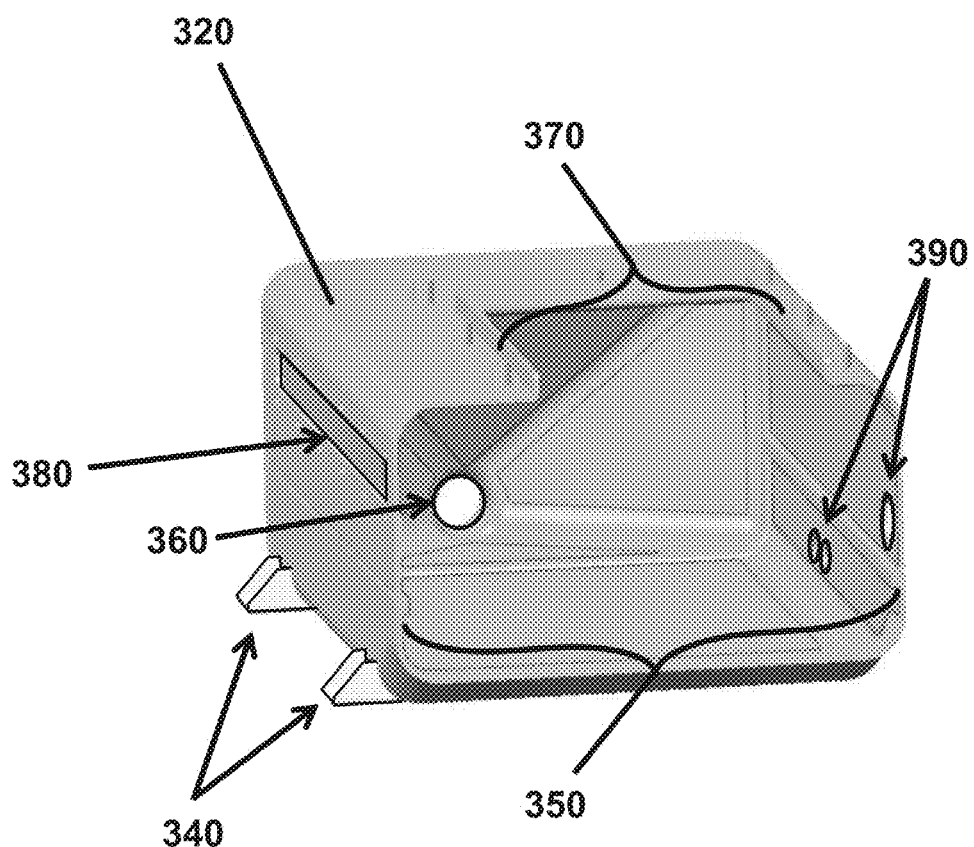
FIG. 7 is a schematic representation of one embodiment of a sample manipulation chamber.

In some cases, a sample manipulation chamber comprises addition openings (access ports) to allow for the entry of additional components (e.g., a sample manipulation arm, wires, cords, etc.) into the chamber (FIG. 4, FIG. 5, FIG. 7). In some cases, in addition to a filter port, an AMS port, and a flow path port, a sample manipulation chamber includes one or more (e.g., 2 or more, 3 or more, 4 or more, 5 or more, 6 or more, etc.) access ports. In some cases, in addition to a filter port, an AMS port, and a flow path port, a sample manipulation chamber includes 1 to 10 additional access ports (e.g., 1 to 9 access ports, 1 to 8 access ports, 1 to 7 access ports, 1 to 6 access ports, 1 to 5 access ports, 1 to 4 access ports, or 1 to 3 access ports).

For example, a sample manipulation chamber can have an access port through which a sample manipulation arm (e.g., a mobile arm such as an automated, i.e., robotic, arm) can penetrate into the sample manipulation chamber. In some cases, an access port is sealed so that the sample manipulation chamber can be penetrated with minimal effect on aerosol containment (e.g., adjustably sealed so that a mobile arm can penetrate into the sample manipulation and move while maintaining aerosol containment). In some cases, a mobile arm (e.g., a sample manipulation arm) can move relative to the sample manipulation chamber in order to manipulate samples, and thus, inside of the chamber. Thus, in some cases, the associated access hole (access port) of the sample manipulation chamber is larger than the dimensions of the mobile arm (at least for the region of the mobile arm that penetrates the sample manipulation chamber). In some cases, in addition to in addition to a filter port, an AMS port, a flow path port, and a sample manipulation arm port, a sample manipulation chamber includes one or more (e.g., 2 or more, 3 or more, 4 or more, 5 or more, 6 or more, etc.) access ports. In some cases, in addition to in addition to a filter port, an AMS port, a flow path port, and a sample manipulation arm port, a sample manipulation chamber includes 1 to 10 additional access ports (e.g., 1 to 9 additional access ports, 1 to 8 additional access ports, 1 to 7 additional access ports, 1 to 6 additional access ports, 1 to 5 additional access ports, 1 to 4 additional access ports, or 1 to 3 additional access ports, 1 to 2 additional access ports, or 1 additional access port).

In some cases, a sample manipulation chamber includes a sample collection vessel (e.g., a tube). Any convenient sample collection vessel can be used. For example, in some cases, a particle collection region includes one or more sample collection tubes (e.g., a single collection tube, 2 or more collection tubes, 3 or more collection tubes, 4 or more collection tubes, 5 or more collection tubes, 6 or more collection tubes, 12 or more collection tubes, 24 or more collection tubes, 48 or more collection tubes, 96 or more collection tubes, 384 or more collection tubes, 1,536 or more collection tubes, etc.). In some cases, a sample collection vessel is a multi-well plate (e.g., a 6-well plate, a 12-well plate, a 24-well plate, a 48-well plate, a 96-well plate, a 384-well plate, a 1,536-well plate, etc.).

The exact dimensions and shape of a sample manipulation chamber can depend on various factors, including the desired features of the sample manipulation chamber, the size and shape of the region enclosed by the sample manipulation chamber (e.g., a particle collection region of a flow cytometer), the size and shape of an instrument with which the sample manipulation chamber is to be associated (e.g., a flow cytometer), etc. One exemplary sample manipulation chamber is 8.7 inches wide, 5 inches high, and 16.2 inches deep.

The width of a sample manipulation chamber can be any convenient width. In some cases (e.g., when the sample manipulation chamber is intended to be associated with a flow cytometer), the width of a sample manipulation chamber can be in a range of from 2 inches to 30 inches (e.g., from 2 inches to 25 inches, from 2 inches to 20 inches, from 2 inches to 15 inches, from 5 inches to 11 inches, from 6 inches to 10 inches, from 7 inches to 10 inches, or from 7 inches to 9 inches).

The height of a sample manipulation chamber can be any convenient height. In some cases (e.g., when the sample manipulation chamber is intended to be associated with a flow cytomter), the height of a sample manipulation chamber can be in a range of from 1 inch to 10 inches (e.g., from 1 inch to 9 inches, from 2 inches to 8 inches, from 3 inches to 7 inches, or from 4 inches to 6 inches).

The depth of a sample manipulation chamber can be any convenient depth. In some cases (e.g., when the sample manipulation chamber is intended to be associated with a flow cytomter), the depth of a sample manipulation chamber can be in a range of from 2 inches to 30 inches (e.g., from 2 inches to 25 inches, from 5 inches to 25 inches, from 8 inches to 24 inches, from 10 inches to 22 inches, from 12 inches to 20 inches, from 14 inches to 18 inches, or from 15 inches to 17 inches).

The volume of a sample manipulation chamber can be any convenient volume. In some cases (e.g., when the sample manipulation chamber is intended to be associated with a flow cytomter), the volume of a sample manipulation chamber can be in a range of from 0.1 cubic feet (cf) to 1 cf (e.g., from 0.2 cf to 0.9 cf, from 0.2 cf to 0.8 cf, from 0.2 cf to 0.7 cf, from 0.2 cf to 0.6 cf, or from 0.3 cf to 0.5 cf).

The exact dimensions and shape of an access hole (an access port) of a sample manipulation chamber can also depend on various factors, including, the size and shape of a component (e.g., a sample manipulation arm, a mobile arm, wires, cords, etc.) that penetrates the chamber, the degree and direction of motion required by a mobile arm that penetrates the chamber, etc. The length, width, and area of an access port are limited in that they can be any dimension that is less than or equal to the length, width, and/or area of the surface of the sample manipulation chamber with which the access port is associated. The shape of an access port of the sample manipulation chamber can be any convenient shape. For example, in some cases, the shape of an access hole of the sample manipulation chamber is selected from: a square, a rectangle, a rectangle with rounded corners, a pentagon, a hexagon, a polygon, an ellipse, a triangle, a trapezoid, a rhomboid, and a circle.

In some cases, a sample manipulation chamber includes a support. For example, in some cases, a sample manipulation chamber includes feet that support the weight of the chamber against a surface (FIG. 7). In some cases, a support of a sample manipulation chamber is a mount, e.g., to allow the sample manipulation chamber to be mounted on a surface. For example, in some cases, a mount can be attached to a sample manipulation chamber, on any surface of the chamber, so that the chamber can be attached to a surface of a flow cytometer (e.g., an inner surface of a flow cytometer).

In cases where a sample manipulation chamber is fluidically coupled to an AMS, when an AMS is actuated, gas (e.g., ambient air, decontamination gas, etc.), in some cases containing aerosols, flows from the filter side of the sample manipulation chamber to the side where the sample chamber is fluidically coupled to the AMS (FIG. 5). Thus, in some cases, the particle collection region can be a mini-environment such that aerosols within the particle collection region are contained and can be carried away by airflow generated by the air filtration system of the AMS. In the example just described, air flows from the particle collection region (e.g., a sample manipulation chamber) to the blower of the AMS. However, (e.g., ambient air, decontamination gas, etc.) can flow in any direction so that aerosols are removed from the targeted region (e.g., the sample manipulation chamber, the particle collection region). Thus, in some embodiments, air flows from the particle collection region to the blower of the AMS; and in some embodiments, air flows from the blower of the AMS to the particle collection region. Various arrangements (e.g., arrangements of blower(s), filter(s), and/or particle collection region(s)) are contemplated and an appropriate arrangement will be based on the desired outcome.

Because the AMS, when present, is a component of the BSH, the dimensions of the AMS are smaller than the dimensions of the BSH, and the exact dimensions and shape of the AMS depend on the dimensions and shape of the BSH. In some cases, the AMS is housed in the BSH (e.g., in an upper region). In some cases, the blower of the AMS is housed in the BSH (e.g., in an upper region) while an associated filter is positioned elsewhere (e.g., behind the main enclosure, inside of the main enclosure, below the main enclosure, etc.). In some cases, the overall volume occupied by the AMS is 20% or less the overall volume occupied by the BSH (e.g., 17.5% or less, 15% or less, 12.5% or less, 10% or less, 7.5% or less, 6% or less, 5% or less, 4% or less, 3% or less, 2% or less, or 1% or less).

The term "fluidically couple" is used herein to mean the coupling of components such that the components are in fluid communication with one another. Thus, two components that are in fluid communication with one another are "fluidically coupled." "Fluids" are liquids and/or gases. For example, two components that are each attached to opposite ends of a hose, where the two components are in fluid communication with one another, are "fluidically coupled" to one another. In cases where a valve is used to restrict flow of a fluid to a particular direction, the two components are still considered to be fluidically coupled. Fluidically coupled components can be coupled in any convenient way. For example, two components can be fluidically coupled directly to one another, or can be fluidically coupled via a conduit (e.g, a hose, a tube, flexible ducting, etc.).

As noted above, in some embodiments, a BSH includes a first (main) air filtration system and an AMS, where the AMS includes a second air filtration system. In some such cases, first and second air filtration systems can be controlled together (e.g., the blower (on/off, speed, etc.) for each can be controlled with the same control). In some embodiments the control can be found on an instrument control panel of the BSH. In some embodiments, the control can be found on an associated processor (e.g., a computer). In some embodiments, the blower of the AMS can operate at two or more speed settings (e.g., low (LO), medium (MED), and/or high (HI)). Speed settings can be set for any convenient speed (e.g., 5 cubic feet per minute (cfm), 10 cfm, 15 cfm, 20 cfm, 25 cfm, 30 cfm, 35 cfm, 40 cfm, 45 cfm, 50 cfm, 55 cfm, 60 cfm, 65 cfm, 70 cfm, 75 cfm, 80 cfm, 85 cfm, 90 cfm, 95 cfm, 100 cfm, 105 cfm, 110 cfm, 115 cfm, 120 cfm, 125 cfm, 130 cfm, 135 cfm, 140 cfm, 145 cfm, 150 cfm, 155 cfm, 160 cfm, 165 cfm, etc.). In some cases, a blower can be controlled by a variable speed setting. For example, in some cases, speed settings can range from 5 cubic feet per minute (cfm) to 300 cfm (from 10 cfm to 200 cfm, from 10 cfm to 150 cfm, from 10 cfm to 100 cfm, from 10 cfm to 80 cfm, from 10 cfm to 60 cfm, from 10 cfm to 50 cfm, from 10 cfm to 40 cfm, or from 15 cfm to 40 cfm).

In some cases, the first and second air filtration systems are independently operable (i.e., can be controlled independently) (e.g., by separate controllers). For example, the blower (on/off, speed, etc.) for the first and second air filtration systems can be controlled with controls dedicated to each air filtration system. In some embodiments the controls can be found on an instrument control panel of the BSH. In some embodiments, the controls can be found on an associated processor (e.g., a computer). In some instances the first and second air filtration systems are physically and fluidically independent. In other words, the two filtration systems can be independently operated without causing negative effects on each other's fluidics system. When one of the filtration systems is turned on, it does not force air through the other filtration system. The first and second filtration systems may be self-contained and self-supporting independent entities. In these embodiments, the systems may be configured to avoid allowing air to be back flushed back into the hood if the main blower is off.

Processor.

In some embodiments, a subject BSH includes a processor. In some cases, a processor allows for user control of an air filtration system (e.g., the first (main) and/or second (redundant) air filtration systems of the BSH). In some embodiments, the processor is configured to receive an input (e.g., an input signal) from the flow cytometer and/or send a signal to the flow cytometer. Such input and output signals provide communication between the flow cytometer instrument and the BSH, e.g., to monitor specific error conditions and take appropriate, safe action if triggered. Various signals and inputs can be sent and/or received, including but not limited to: a signal reporting the status of a particular flow cytometric procedure (e.g., a cleaning procedure, a sorting procedure, etc.); a signal reporting the air flow rate (e.g., the air flow rate generated by at least one air filtration system of a BSH); a signal reporting the time remaining or time elapsed for a particular flow cytometric procedure; an error signal (e.g., an error signal generated in response to a clog in the flow path of the flow cytometer, an error signal generated by a sub-threshold air flow rate of an air filtration system); etc.

In some embodiments, an error signal is sent to the flow cytometer and/or received from the flow cytometer. In some cases, a processor of the BSH sends an error signal to the flow cytometer when the airflow (generated by at one or more of the air filtration systems) falls below a pre-determined threshold. In some cases, the error signal alerts the user to stop and/or pause sample flow through the flow path during a flow cytometric procedure (e.g, in order to reduce and/or halt the production of aerosols). In some cases, the error signal instructs to the flow cytometer to automatically stop and/or pause sample flow through the flow path during a flow cytometric procedure. Error signals sent from the flow cytometer to the BSH can be useful, for example, in cases where a threshold level of air flow is required to safely remove aerosols during a flow cytometric procedure. In this way, when the cytometer sort head has an error (e.g., by a clog in the line, a faulty motor, a leak, etc.), the cytometer can send a signal to the BSH to increase airflow (e.g., when a clogged line is flushed out, increased amounts of particles can be generated that need to be evacuated).

Signals can be generated in a variety of different ways. In some cases, signals are generated by detectors/sensors that detect and report the status of particular parameters (e.g., the air flow rate being generated by one or more air filtration systems of a BSH, the flow rate of the flow path of a flow cytometer, etc.).

Instrument Control Panel.

Figure 6:
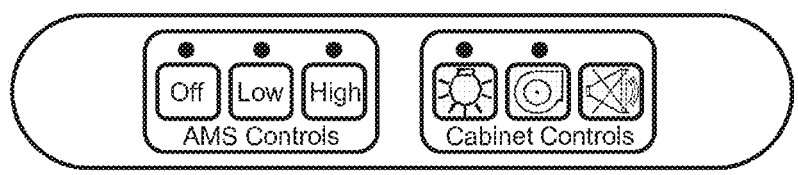
FIG. 6 is a schematic representation of one example of an instrument control panel of a biosafety hood (BSH).

In some embodiments, a BSH has an instrument control panel. An instrument control panel includes a processor to allow a user to control a feature of the BSH. In some embodiments, the instrument control panel is configured to allow a user to control the first (main) and/or second (redundant) air filtration systems of the BSH. In some cases, a BSH instrument control panel is configured to allow a user to control one or more steps of a decontamination procedure (described in more detail below). In some embodiments, the AMS evacuates the particle collection region (e.g., sample manipulation chamber) and its operation can be controlled separately from the main system blower. In some embodiments, the instrument control panel will have controls (e.g., a dial, buttons, etc.) for actuating the blower of the AMS at two or more speed settings (e.g., LO for 15 cfm, and HI for 40 cfm) (FIG. 6).

Decontamination.

In some embodiments, a subject BSH is configured to perform a decontamination procedure. The term "decontamination procedure" is used herein to refer to a procedure that results in decontamination of the main enclosure (which, as described above, can be defined by surfaces of both the BSH and the flow cytometer instrument base, or can be defined solely by surfaces of the BSH). Decontamination can be performed manually, or various steps (or all steps) of decontamination can be performed in an automated manner (i.e., controlled by a processor). In some cases, the duration of at least one processor-controlled step of the decontamination procedure can be input into a processor by a user. Any convenient type of decontamination procedure can be performed. For example, decontamination procedures can include the use of ultraviolet (UV) light, decontaminating fluids, decontamination gases, etc.

In some embodiments, steps of a decontamination procedure include: (a) sealing the main enclosure to create a mini-environment comprising the flow cytometer; (b) introducing a decontamination gas into the mini-environment; and (c) removing the decontamination gas from the mini-environment.

Regarding step (a), as described above, the BSH and the flow cytometer instrument base can be attached in an air tight manner so that aerosols do not escape where surfaces of the BSH and instrument base meet. Instead aerosols are directed out of the main enclosure by the air filtration system(s) of the BSH. The step of sealing the main enclosure to create a mini-environment refers to the step of forming the air tight seals. For example, if rubber gaskets are used where the BSH and instrument base meet, sealing the main enclosure may encompass locking down clamps to assure a tight seal. As described above, in some embodiments, a subject BSH has a moveable panel (e.g., a sliding sash) that can be closed. In some such cases, the step of sealing the main enclosure to create a mini-environment includes closing the moveable panel in such a way that an air tight seal is formed (e.g., using locking clamps, simply sliding a sash into a locked position, using an automated locking and sealing mechanism, etc.).

Step (b), the step of introducing a decontamination gas into the mini-environment, refers to the controlled introduction of a known gas into the mini-environment. Any convenient decontamination gas can be used. In some embodiments, the decontamination gas is a sterilizer. The term "sterilizer" is used herein as it is defined by the United States Environmental Protection Agency (U.S. EPA): an antimicrobial pesticide that destroys or eliminates all forms of microbial life in the inanimate environment (including all forms of vegetative bacteria, bacterial spores, fungi, fungal spores, and viruses). Since sterilization includes eradication of all living microorganisms, such claims are intrinsically related to protection of human health. A list of substances considered to be sterilizers by the EPA (and are therefore suitable as decontamination gases when present in gaseous form) includes: (i) Hydrogen peroxide (e.g., 1%, 31%, 35%, 59%, 70%); (ii) hydrogen peroxide/enthaneperoxic acid (e.g., 1%/0.8%, 5.6%/0.3%, 22%/4.5%, 22%/15%, 24%/1.2%, 27%/2%, 27.5%/5.8%); (iii) hydrogen peroxide/enthaneperoxic acid/caprylic acid (e.g., 6.9%/4.4%/3.3%); (iv) sodium chlorite (e.g., 0.85%, 1.52%, 25%, 37%, 72.8%); (v) tetraacetylethylenediamine (e.g., 61.6%), 2,4-Dodecadienoic acid, 3,7,11-trimethyl-ethyl ester, (S-(E,E)) (e.g., 95%); (vi) 1-Decanaminium, N-decyl-N,N-dimethyl-chloride/Alkyl* dimethyl benzyl ammonium chloride *(50%014, 40% C12, 10% C16)/1-Octanaminium, N,Ndimethyl-N-octyl-chloride/1-Decanaminium, N,N-dimethyl-N-octyl-chloride (e.g., 0.06%/0.16%/0.06%/0.12%); (vii) ethylene oxide (e.g., 8.5%, 8.6%, 10%, 12%, 20%, 80%, 89.4%, 90%, 96%, 97%, 98.06%, 100%); (viii) sodium hypochlorite (e.g., 12.5%); (ix) Alkyl* dimethyl benzyl ammonium chloride *(50%014, 40% C12, 10% C16) (e.g., 0.3%); (x) sodium chlorite/sodium dichloroisocyanurate dehydrate (e.g., 20.8%/7%); (xi) silver (e.g., 0.03%, 0.78%, 17.5%); (xii) chloroxylenol (e.g., 4.51%); and (xiii) Tetrakis (hydroxymethyl)phosphonium sulphate (THPS)/Alkyl* dimethyl benzyl ammonium chloride *(50%012, 30% C14, 17% C16, 3% C18) (e.g, 0.3%/0.5%). The preceding list of sterilizers was extracted from a table generated by the EPA in December 2011 entitled: "List A: Antimicrobial Products Registered with the EPA as Sterilizers".

In some embodiments, the decontamination gas is vaporized hydrogen peroxide (VHP). VHP can be produced from a solution of liquid hydrogen peroxide ($H_2O_2$) and water, in some cases using generators specifically designed for the purpose. Such generators initially dehumidify the ambient air, then produce VHP by passing aqueous hydrogen peroxide over a vaporizer, and circulate the vapor at a programmed concentration in the air. Various mixtures can be used and VHP can be used at a variety of concentrations (see list of sterilizers above). VHP is typically circulated at a concentration range from 140 parts per million (ppm) to 1400 ppm, which can depend on the infectious agent to be cleared. After the VHP has circulated in the enclosed space for a pre-defined period of time, it can be re-collected, where it can be broken down into water and oxygen by a catalytic converter, until concentrations of VHP fall to safe levels (typically <1 ppm). Alternatively, the VHP can be vented to the outside air, in cases where recapturing of the VHP is not desired and/or needed.

In some embodiments, the decontamination gas is chlorine dioxide gas (i.e., gaseous chlorine dioxide). For information regarding the use of chlorine dioxide gas, refer to U.S. patent application US20080286147, which is hereby incorporated by reference in its entirety.

In some embodiments, a gas source is used. A suitable gas source can be any gas-containing container in fluid communication with the mini-environment. In some cases, the gas source is pressurized so that gas will flow from the gas source to the mini-environment. In some cases, the gas source includes an engine (e.g., the gas source is motorized) that can generate air flow from the gas source to the mini-environment. In some cases, the gas source can produce particular formulations of gas mixtures prior to, or during, introduction of the mixture into the mini-environment. In some cases, the gas source includes a humidifier. In some cases, the gas source is portable (e.g., removable). In some cases, the gas source can be stored in the flow cytometer instrument base. In some embodiments, the introduction of decontamination gas into the mini-environment includes a step of actuating a gas source (e.g., opening a valve to allow fluid communication between the gas source and the mini-environment, actuating a motor or utilizing pressure to induced gas flow, etc.).

The decontamination gas is allowed to remain in the mini-environment for a period of time sufficient to provide the desired level of decontamination, and such periods of time (exposure times) will be depend on many factors including temperature, air flow, volume of the mini-environment, formulation and concentration of the gas, suspected level of contamination, etc.

Step (C), the step of removing the decontamination gas from the mini-environment can be performed by any convenient method. For example, in some cases, the decontamination gas can be blown out of the mini-environment using the blower of the first (main) air filtration system of the BSH. In some such cases, an air filter is used and in some such cases, an air filter is not used. In some embodiments, the decontamination gas can be re-collected (e.g., for re-use, for discarding, for hazardous waste pick-up, for catalytic conversion to a safer variety of gas, etc.), or neutralized.

In some embodiments, a decontamination procedure includes a step of modulating flow of the decontamination gas (e.g., circulating the decontamination gas) within the mini-environment, thus increasing exposure of surfaces to the decontamination gas. In some embodiments, modulating flow includes actuating an air filtration system (e.g., actuating the blower of the main air filtration system and/or the blower of the AMS). In some cases, modulating flow includes alternatively, and repeatedly actuating the blower of the main air filtration system and actuating the blower of the AMS (e.g., "pulsing" the blowers of the air filtration systems). In some cases, the evacuation ports of the air filtration systems are closed and the decontamination gas is re-circulated during the step of modulating flow. In some cases, the evacuation ports of the air filtration systems are open during the step of modulating flow, and decontamination gas is continually added to the mini-environment, thus creating a flow of decontamination gas from the gas source to the evacuation port.

Flow Cytometer Instrument Base

In some embodiments, the present disclosure provides a "flow cytometer instrument base", also referred to herein simply as an "instrument base". A subject flow cytometer instrument base supports the weight of a flow cytometer and provides a surface with which a flow cytometer can associate. For example, a subject instrument base can provide an upward facing surface upon which a flow cytometer can rest. The flow cytometer can be attached to the instrument base, or can simply rest upon the instrument base, being held in place by the force of gravity. Alternatively, a subject instrument base can provide a weight-bearing, non-upward facing surface to which a flow cytometer can attach. In cases where the flow cytometer attaches to the instrument base, any convenient type of attachment (e.g., bolts, clamps, pegs, latches, screws, magnets, adhesives, and the like) can be used. Thus, in some cases, the instrument base is configured to attach to a flow cytometer, and/or the flow cytometer is configured to attach to the instrument base (see "enclosure" above). In yet other instances, a flow cytometer may be integrated, at least partially, with an instrument base, e.g., where certain fluidics and/or electronics of the flow cytometer are integrated into one portion of the base, and the sort head/optics are integrated into another portion of the base. In these instances, the integrated flow cytometer and cytometer instrument base may include: a cytometer base which includes an cytometer electronics component, e.g., drawer that houses the laser(s) and cytometer processing functionalities, and a fluidics component, e.g., drawer, that houses the supporting fluids. On top of the base may be the cytometer sort head, sort housing or sort area, which house the optics, sort chamber, and sample line.

The exact dimensions and shape of the instrument base will vary based on the dimensions of the flow cytometer to be enclosed, and/or based on the BSH to which the instrument may attach. Generally, a suitable instrument base can be any shape and/or size as long as the instrument base can attach to a BSH such that the main enclosure is large enough to contain a flow cytometer. An instrument base can support the weight of a flow cytometer and a BSH.

In some embodiments, the height of the instrument base is in a range of from 1 foot (ft) to 5 ft (e.g., from 2 ft to 4 ft, from 2.5 ft to 3.5 ft, from 3 ft to 3.5 ft, 2 ft, 2.5 ft, 3 ft, 3.5 ft, 4 ft, 4.5 ft, or 5 ft).

In some cases, the width of the instrument base is in a range of from 2 feet (ft) to 10 feet (ft) (e.g., from 2 ft to 9 ft, from 2 ft to 8 ft, from 2 ft to 7 ft, from 2 ft to 6 ft, from 2 ft to 5 ft, from 2 ft to 4 ft, from 2 ft to 3 ft, from 3 ft to 5 ft, from 3.5 ft to 5.5 ft, from 3 ft to 4 ft, 2 ft, 3 ft, 4 ft, 5 ft, 6 ft, 7 ft, 8 ft, 9 ft, or 10 ft, etc.). Because the instrument base is designed to support a flow cytometer, the width of the instrument base is equal to or greater than the width of the flow cytometer. In some cases, the width of the instrument base is in a range of from 100.05% to 250% the width of the flow cytometer to which the instrument is to be associated (e.g., from 100.05% to 225%, from 100.05% to 200%, from 100.05% to 175%, from 100.05% to 170%, from 100.05% to 165%, from 100.05% to 160%, from 100.05% to 150%, from 100.05% to 140%, from 100.05% to 130%, from 100.05% to 125%, from 100.05% to 120%, from 100.05% to 115%, from 100.05% to 110%, from 100.05% to 107.5%, from 100.05% to 105%, or from 100.05% to 102.5%).

In some cases, the depth of the instrument base is in a range of from 2 feet (ft) to 10 feet (ft) (e.g., from 2 ft to 9 ft, from 2 ft to 8 ft, from 2 ft to 7 ft, from 2 ft to 6 ft, from 2 ft to 5 ft, from 2 ft to 4 ft, from 2 ft to 3 ft, from 3 ft to 5 ft, from 3.5 ft to 5.5 ft, from 3 ft to 4 ft, 2 ft, 3 ft, 4 ft, 5 ft, 6 ft, 7 ft, 8 ft, 9 ft, or 10 ft, etc.). Because the instrument base is designed to support a flow cytometer, the depth of the instrument base is equal to or greater than the depth of the flow cytometer. In some cases, the depth of the instrument base is in a range of from 100.05% to 250% the depth of the flow cytometer to which the instrument is to be associated (e.g., from 100.05% to 225%, from 100.05% to 200%, from 100.05% to 175%, from 100.05% to 170%, from 100.05% to 165%, from 100.05% to 160%, from 100.05% to 150%, from 100.05% to 140%, from 100.05% to 130%, from 100.05% to 125%, from 100.05% to 122.5%, from 100.05% to 120%, from 100.05% to 115%, from 100.05% to 110%, from 100.05% to 107.5%, from 100.05% to 105%, or from 100.05% to 102.5%).

Fluid Source.

In some embodiments, a flow cytometer instrument base includes a fluid source (e.g., a gas or liquid source). In some cases, the fluid source may be sealed to maintain sterility of the contained fluid. For example, the fluid source may be closed to the surrounding environment to prevent undesired contact between the fluid and the surrounding environment. Although the fluid source may be sealed from the surrounding environment, the fluid source may include one or more ports, such as one or more inlets and/or outlets. The one or more ports may be configured to permit access to the interior of the fluid source when desired. For example, the fluid source may include an inlet configured to allow a fluid, such as a sample fluid, reagent, wash buffer etc. to be added to the fluid source. In some cases, the fluid source includes an outlet configured to allow fluid from the fluid source to be removed from the fluid source. The ports may be self-sealing ports, such that fluid can be added or removed from the fluid source, for example using a syringe, and then the port seals itself to prevent contact between the fluid in the fluid source and the surrounding environment.

In some instances, the fluid source includes a fluid outlet. The fluid outlet may be configured to carry the fluid as the fluid flows out of the fluid source. The fluid outlet may be in fluid communication (fluidically coupled) with a flow cytometer. The fluid outlet may be in fluid communication with a mini-environment, where the mini-environment is created by sealing the main enclosure of a subject flow cytometer system (e.g., where BSH and instrument base are attached). In some cases, the fluid source is directly connected to the component with which it is in fluidic communication. In other embodiments, the fluid source is connected to the component with which it is in fluidic communication via a conduit (e.g., a hose, tubing, flexible ducting, etc.). In some cases, the fluid source further includes a clamp. The clamp may be configured to block the flow of fluid from the fluid source. For instance, the clamp may be positioned around the conduit. When configured in a closed position, the clamp substantially blocks the conduit, for example by pinching the conduit to occlude the inner lumen, and thus preventing fluid from flowing through the conduit. When configured in an open position, the clamp does not block the flow of fluid through the conduit.

In some embodiments, the fluid source is made of a polymer, such as, but not limited to, polyvinyl chloride (PVC), ethyl vinyl acetate (EVA), polyethylene, polypropylene, combinations thereof, and the like.

In certain embodiments, the fluid source includes one chamber that includes the fluid. In other cases, the fluid source includes two or more chambers. The two or more chambers may contain the same or different fluids. For example, a first fluid source chamber may contain a first fluid and a second fluid source chamber may contain a second fluid. A fluid source comprising two or more chambers may facilitate the mixing of fluids, where the first sample fluid is contained in the first fluid source chamber and the second sample fluid is contained in the second fluid source chamber. The two or more chambers may be configured to be in fluid communication with a single conduit or with two or more conduits, as desired. For instance, the two or more chambers may be in fluid communication with one conduit. The lumens of the two or more chambers may be joined together at a Y-connector, a valve (e.g., a pinch valve), or the like.

In some cases, the instrument base has a door or removable panel to allow user access to a fluid source. In some cases, the fluid source is removable (i.e., the fluid source can be removed from the instrument base). In In some embodiments, the instrument base has a support for the fluid source. In some embodiments, the support is extendible (e.g., at least partially extendible) away from the body of the instrument base to allow user access to the fluid source. In some cases, the extendible support for the fluid source is a drawer.

As described above, a suitable flow cytometer instrument base can attach to a biosafety hood (BSH). In some embodiments, a flow cytometer has non-aerosol generating components that are not part of the sample flow path and are not contained by the enclosure of the BSH. For example, components such as spectral filters, lasers, detector arrays, etc. can be housed outside of the main enclosure and/or outside of the BSH. For example, in some embodiments, a flow cytometer instrument base contains non-aerosol generating components (e.g., spectral filters, lasers, detector arrays, and the like) of an associated flow cytometer (FIG. 3C).

Flow Cytometer

In some embodiments, the present disclosure provides a flow cytometer. Flow cytometry is a well-known methodology using multi-parameter data for identifying and distinguishing between different particle types (i.e., particles, such as cells, that vary from one another in terms of label wavelength, label intensity, size, etc.) in a fluid medium. In general, a flow cytometer is made up of at least three regions: (i) a sample loading region; (ii) a particle interrogation region; and (iii) a particle collection region (e.g., a sample manipulation chamber).

In performing flow cytometry (i.e., flow cytometrically analyzing particles of a sample), a liquid sample (containing particles to be analyzed) is first introduced into a sample loading region, which is sometimes referred to in the art as a sample injection chamber, of a flow cytometer. During sample acquisition, the chamber of the sample loading region is pressurized to force sample into the flow path of the flow cytometer, toward the particle interrogation region. Ideally, the fluid stream is at its minimum diameter so that cells pass through the laser beam of the sample interrogation region in a single-file stream. However, depending on the application, a lower resolution might be acceptable in order to acquire data more quickly.

When in the flow path, articles are passed substantially one at a time through the particle interrogation region, where each of the particles is exposed individually to an energy source (e.g., a light source) and measurements of light scatter parameters (e.g., forward scatter, side scatter, etc.) and/or fluorescent emissions as desired (e.g., one or more fluorescent emissions) are separately recorded for each particle. The energy source may include an illuminator that emits light of a single wavelength, such as that provided by a laser (e.g., He/Ne or argon) or a mercury arc lamp with appropriate filters. Examples of excitation light sources include lasers, light emitting diodes, and arc lamps. For example, light at 488 nm may be used as a wavelength of emission in a flow cytometer having a single sensing region. For flow cytometers that emit light at two or more distinct wavelengths, additional wavelengths of emission light may be employed, where specific wavelengths of interest typically include, but are not limited to: 535 nm, 635 nm, and the like. A subject flow cytometer can have one or more lasers (e.g., two or more, three or more, four or more, five or more, six or more, etc.).

In the particle interrogation region, detectors (e.g., light collectors, such as photomultiplier tubes (or "PMT")), are used to record light that passes through each particle (generally referred to as forward light scatter), light that is reflected orthogonal to the direction of the flow of the particles through the sensing region (generally referred to as orthogonal or side light scatter) and fluorescent light emitted from the particles, if it is labeled with fluorescent marker(s), as the particle passes through the sensing region and is illuminated by the energy source. Each of forward light scatter (or FSC), orthogonal light scatter (SSC), and fluorescence emissions (FL1, FL2, etc.) comprise a separate parameter for each particle (or each "event"). Thus, for example, two, three or four parameters can be collected (and recorded) from a particle labeled with two different fluorescence markers.

The data recorded for each particle is analyzed in real time and/or stored in a data storage and analysis device, such as a computer, as desired. Publications from the scientific and patent literature describing various designs, configurations, and uses of flow cytometers include, for example: (i) Jaye et al., J Immunol. 2012 May 15; 188(10):4715-9: Translational applications of flow cytometry in clinical practice; (ii) Krutzik et al., Curr Protoc Cytom. 2011 January; Chapter 6:Unit 6.31: Fluorescent cell barcoding for multiplex flow cytometry; (iii) Black et al., Assay Drug Dev Technol. 2011 February; 9(1):13-20: Cell-based screening using high-throughput flow cytometryl (iv) Abayomi et al., Cytometry B Clin Cytom. 2008; 74 Suppl 1:S80-9: Flow cytometry as the spearhead for delivering sustainable and versatile laboratory services to HIV-burdened health care systems of the developing world: a Caribbean model; (v) Snow et al., Cytometry A. 2004 February; 57(2):63-9: Flow cytometer electronics; (vi) Schmid et al., Cytometry A. 2003 December; 56(2):113-9: Biosafety concerns for shared flow cytometry core facilities; and (vii) U.S. Pat. Nos. 8,502,976, 8,486,371, 8,441,637, 8,441,624, 7,990,525, 8,021,872, 7,611,849, and 7,354,773; all of which citations are hereby incorporated by reference in their entirety.

Any convenient flow cytometer is suitable for use in a subject flow cytometer system, and an appropriate flow cytometer will be based on the desired features of the flow cytometer. For example, some flow cytometers are designed to interrogate particles for various characters (e.g., forward light scatter, side light scatter, fluorescence, etc.), but cannot sort the particles as they flow through the machine. Some flow cytometers are equipped to sort particles as they flow through the machine, redirecting the particle (after the particle has been interrogated/evaluated) to a particular location (e.g., into a desired sample collection container).

During sorting, the fluid stream is broken into highly uniform droplets, which detach from the stream. The time between when a particle intercepts the energy source (e.g., the laser) and when it reaches the droplet breakoff point is determined. When a particle is detected that meets the predefined sorting criteria, an electrical charge is applied to the stream just as the droplet containing that particle breaks off from the stream. Once broken off from the stream, the droplet—now surrounded by air—retains its charge. The charged droplet passes by two strongly charged deflection plates. Electrostatic attraction and repulsion cause each charged droplet to be deflected to the left or right, depending on the droplet's charge polarity. For example, in some cases, a flow cytometer can sort particles into one of two different tubes, or into a desired well of a multi-well plate (e.g., a 6-well plate, a 12-well plate, a 24-well plate, a 48-well plate, a 96-well plate, etc.). Uncharged droplets are not affected by the electric field and pass down the center to be collected or aspirated as waste.

Examples of suitable flow cytometers include, but are not limited to flow cytometers manufactured by Becton, Dickinson and Company, including: BD ACCURI™ C6, BD FACSCANTO™, BD FACSVERSE™, BD LSRFORTESSA™ X-20, BD LSRFORTESSA™, BD INFLUX™, BD FACSJAZZ™, BD FACSARIA™ (e.g., BD FACSARIA™ III), and the flow cytometer provided with the BD FACSARIA™ Fusion.

Regardless of the type of flow cytometer, the term "particle collection region" as used herein refers to the region of the flow cytometer where the flow path comes to an end. In some cases, particles are sorted and/or collected in the particle collection region. In some cases, particles are collected as waste or discarded (e.g., aspirated) in the particle collection region.

While aerosols may be generated anywhere along the flow path of a flow cytometer, the majority of aerosols tend to be generated in the particle collection region. Thus, in some embodiments, the particle collection region is configured to fluidically couple (e.g., via a conduit, such as a hose, a tube, flexible ducting, etc.) to a dedicated air filtration system referred to herein as an aerosol management system (AMS) (described in more detail above). In some such cases, the particle collection region is an enclosed chamber (a sample manipulation chamber)(FIG. 3 B, FIG. 4, FIG. 5, and FIG. 7), with exceptions that the sample manipulation chamber can include: (i) an opening (a filter port) for a filter on one side to allow clean air into the sample manipulation chamber; (ii) an opening (an AMS port) on one side that can fluidically couple to an AMS, e.g., the opening can be connected to a conduit (e.g., a hose, flexible tubing, flexible ducting, etc.) that can connect to an AMS (FIG. 4), which generates air flow; and (iii) an opening (a flow path port) to allow the flow path of the flow cytometer to enter the sample manipulation chamber. In some cases, a sample manipulation chamber includes additional access ports (described in more detail above).

When the AMS is actuated, gas (e.g., ambient air, decontamination gas, etc.), in some cases containing aerosols, flows from the filter side of a sample manipulation chamber to the side where the sample manipulation chamber is fluidically coupled to the AMS (FIG. 5). Thus, in some cases, the particle collection region can be a mini-environment such that aerosols within the particle collection region are contained and can be carried away by airflow generated by the air filtration system of the AMS. In some embodiments, the sample manipulation chamber of the particle collection region can be opened (e.g., via a hinged door, a sliding door, etc.) to allow operator access to the sample manipulation chamber (e.g., to recover sorted samples, for cleaning, to allow gas exposure during decontamination procedures, etc.) (FIG. 3B).

One non-limiting example of a flow cytometer having a particle collection region (e.g., a sample manipulation chamber) configured to fluidically couple to an aerosol management system of a biosafety hood is the flow cytometer provided with the BD FACSARIA™ Fusion, which is commercially available from Becton, Dickinson and Company.

In some embodiments, a flow cytometer has non-aerosol generating components that are not part of the sample flow path and are not contained by the enclosure of the BSH. For example, components such as spectral filters, lasers, detector arrays, etc. can be housed outside of the enclosure of the BSH. For example, in some embodiments, a flow cytometer instrument base contains non-aerosol generating components (e.g., spectral filters, lasers, detector arrays, and the like) of an associated flow cytometer (FIG. 3C).

The exact dimensions and shape of the flow cytometer will depend on the desired features of the flow cytometer, as well as the dimensions and shape of the BSH and/or instrument base with which the flow cytometer is to be associated.

In some embodiments, the volume of the flow cytometer (i.e., the volume occupied) is in a range of from 15 cubic feet (cf) to 60 cf (e.g., 15 cf to 50 cf, 15 cf to 40 cf, 15 cf to 35 cf, 15 cf to 30 cf, 17.5 cf to 35 cf, 17.5 cf to 30 cf, 17.5 cf to 27.5 cf, 17.5 cf to 25 cf, or 20 cf to 22.5 cf).

In some embodiments, the height of the flow cytometer is in a range of from 1 foot (ft) to 6 feet (ft) (e.g., from 1.5 ft to 5 ft, from 1.5 ft to 4 ft, from 1.5 ft to 3 ft, from 1.5 ft to 2.5 ft, from 2 ft to 5 ft, from 2 ft to 4 ft, from 2 ft to 3 ft, from 2 ft to 2.5 ft, 2 ft, 2.1 ft, 2.2 ft, 2.3 ft, 2.4 ft, 2.5 ft, 3 ft, 4 ft, or 5 ft).

In some cases, the width of the flow cytometer is in a range of from 2 feet (ft) to 10 feet (ft) (e.g., from 2 ft to 9 ft, from 2 ft to 8 ft, from 2 ft to 7 ft, from 2 ft to 6 ft, from 2 ft to 5 ft, from 2 ft to 4 ft, from 2 ft to 9 ft, from 2.5 ft to 8 ft, from 2.5 ft to 7 ft, from 2.5 ft to 6 ft, from 2.5 ft to 5 ft, from 2.5 ft to 4.5 ft, from 2.5 ft to 4 ft, from 3 ft to 9 ft, from 3 ft to 8 ft, from 3 ft to 7 ft, from 3 ft to 6 ft, from 3 ft to 5 ft, from 3 ft to 4.5 ft, from 3 ft to 4 ft, from 3.5 ft to 9 ft, from 3.5 ft to 8 ft, from 3.5 ft to 7 ft, from 3.5 ft to 6 ft, from 3.5 ft to 5 ft, from 3.5 ft to 4.5 ft, from 3.5 ft to 4 ft, 2 ft, 3 ft, 3.5 ft, 4 ft, 4.5 ft, 5 ft, 6 ft, 7 ft, 8 ft, 9 ft, or 10 ft).

In some cases, the depth of the flow cytometer is in a range of from 1 foot (ft) to 6 feet (ft) (e.g., from 1.5 ft to 5 ft, from 1.5 ft to 4 ft, from 1.5 ft to 3 ft, from 1.5 ft to 2.5 ft, from 2 ft to 5 ft, from 2 ft to 4 ft, from 2 ft to 3 ft, from 2 ft to 2.5 ft, 2 ft, 2.1 ft, 2.2 ft, 2.3 ft, 2.4 ft, 2.5 ft, 3 ft, 4 ft, or 5 ft).

Figure 2:
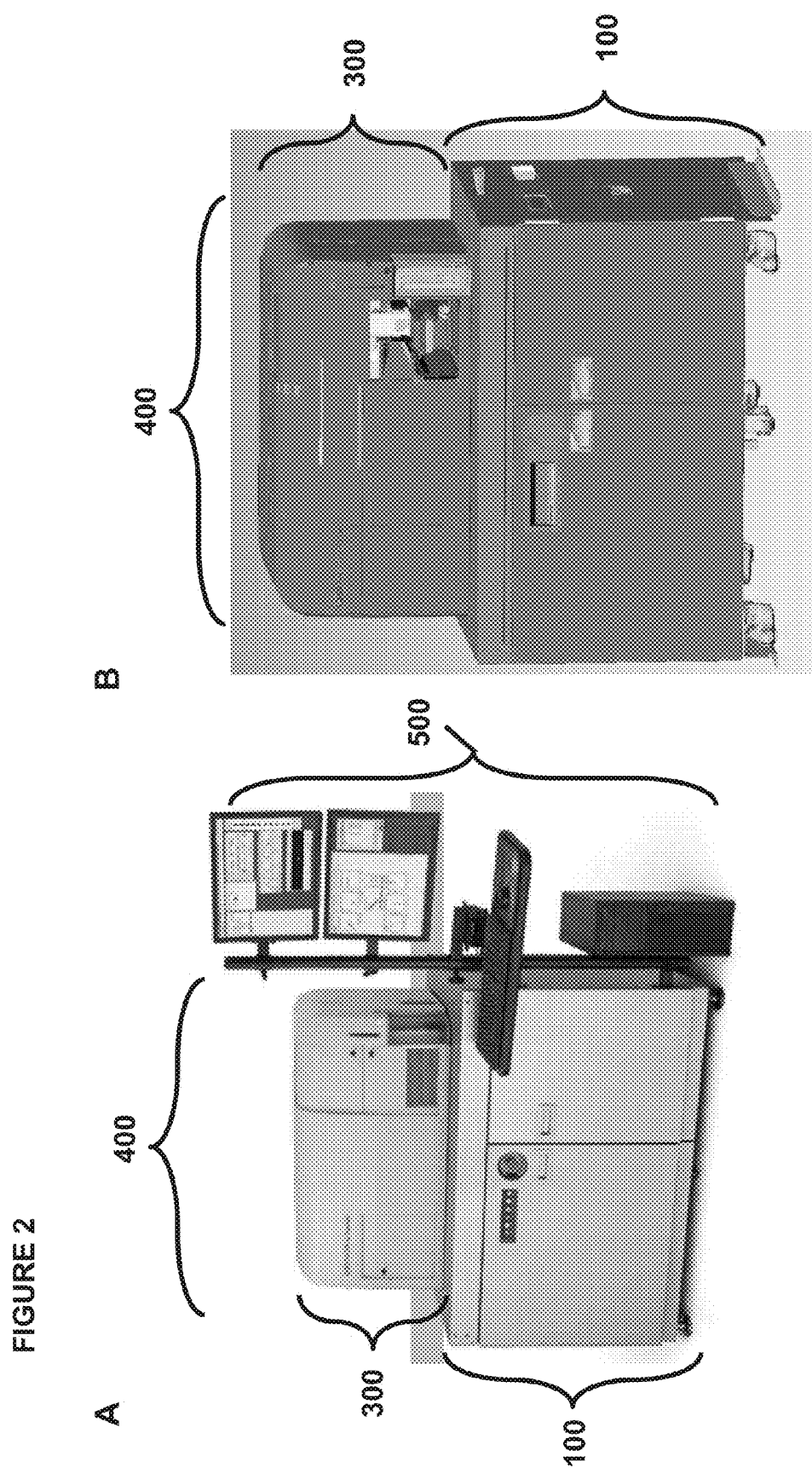
FIG. 2 panels A-B depict one embodiment of a flow cytometer system 400 that includes a flow cytometer instrument base 100, and a flow cytometer 300.

An example of an embodiment of a flow cytometry system according to the present disclosure is shown in the schematic illustrations and pictures presented in FIGS. 1 and 2. A flow cytometry system 400 can include any combination of three main components: a flow cytometer instrument base 100, a biosafety hood (BSH) 200, and a flow cytometer 300. FIG. 1 shows a flow cytometer system 400 that includes the three components: a flow cytometer instrument base 100, a BSH 200, and a flow cytometer 300. FIG. 2 shows a flow cytometer system 400 that includes two of the three components: a flow cytometer instrument base 100, and a flow cytometer 300. A BSH can be added to the flow cytometer system of FIG. 2 at any time. Thus, the instrument base 100 of FIG. 2 can be configured to attach to a subject BSH. The flow cytometer systems of FIGS. 1A and 2A also include a processor, which in the depicted embodiment is part of an entire computer workstation 500.

Figure 3:
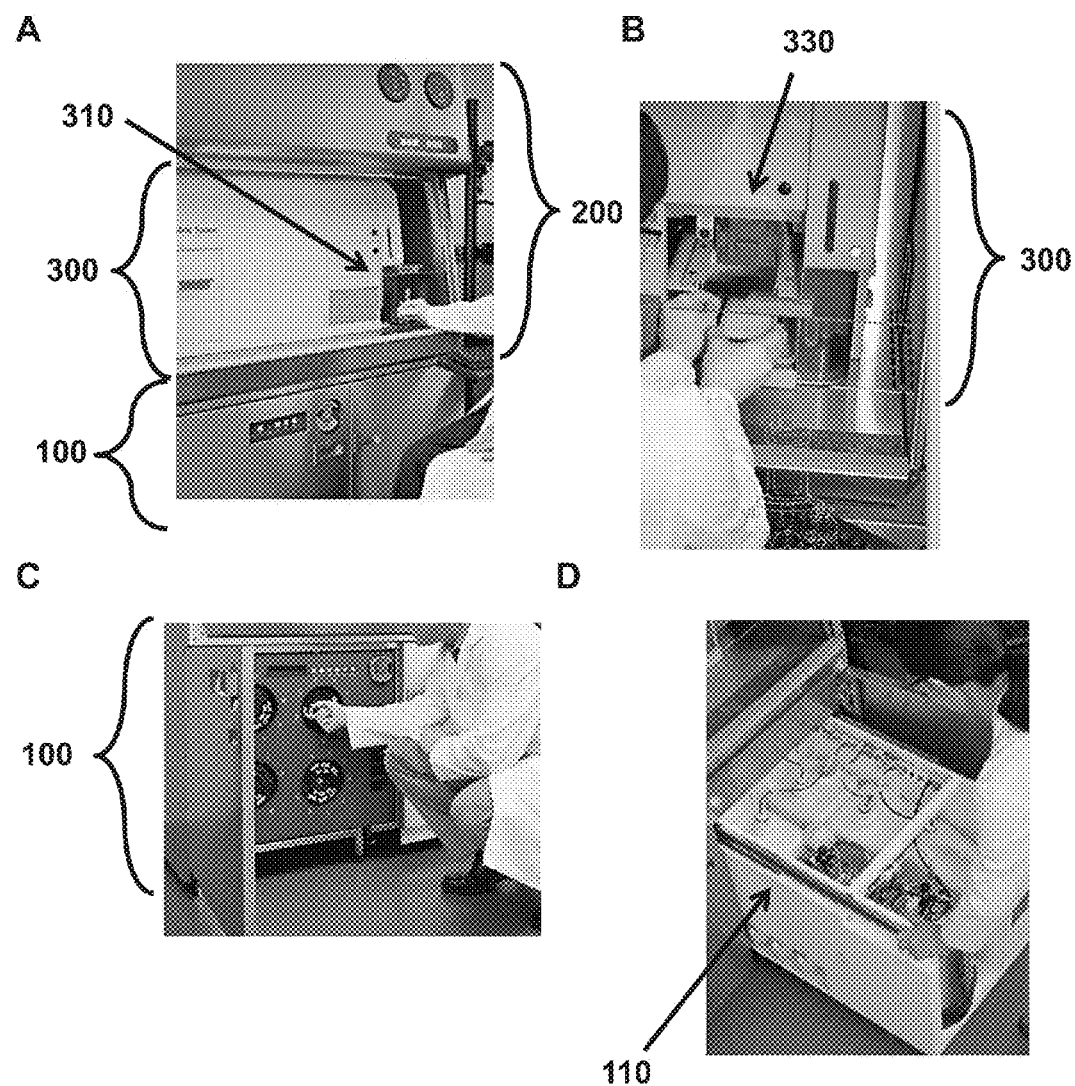
FIG. 3 panels A-D depict various components and various embodiments of a flow cytometer system.

FIG. 3 depicts various components and various embodiments of a flow cytometer system. FIG. 3A depicts a step of introducing a sample into a sample loading region 310 of a flow cytometer 300 of a subject flow cytometer system that includes a flow cytometer instrument base 100, and biosafety hood (BSH) 200. Depicted is a user inserting a sample into the sample loading region. FIG. 3B depicts an operator (i.e., a user) manipulating a sample within a particle collection region (a sample manipulation chamber) 330 of a flow cytometer 300, where the flow cytometer system includes a BSH. A sash on the front of the BSH is pulled down so that only a small space exists where the user is extending their arms into the main enclosure. In the depicted embodiment, the particle collection region (a sample manipulation chamber) 330 has been opened to allow the user access. While performing a cytometric procedure, the particle collection region (a sample manipulation chamber) 330 can be closed to in order to trap aerosols generated during the procedure. Thus, the particle collection region 330 depicted can be an enclosed sample manipulation chamber with exceptions that there can be (i) an opening (a filter port) for a filter on one side to allow clean air into the sample manipulation chamber; (ii) an opening (an AMS port) on one side that can fluidically couple to an AMS, e.g., the opening can be connected to a conduit (e.g., a hose, flexible tubing, flexible ducting, etc.) that can connect to an AMS (FIG. 4), which generates air flow; and (iii) an opening (a flow path port) to allow the flow path of the flow cytometer to enter the sample manipulation chamber. An optional AMS can be included in the BSH such that aerosols generated in the particle collection region (a sample manipulation chamber) 330 are removed by the air flow generated by the blower of the AMS.

FIG. 3C depicts a flow cytometer instrument base 100 that houses detector arrays of an associated flow cytometer. In the depicted embodiment, the flow cytometer has non-aerosol generating components (octagon detector arrays), which are not part of the sample flow path, do not generate aerosols, and are not contained by the enclosure of the BSH. Instead, the components are contained in the flow cytometer instrument base 100. As discussed above, the phrase "the flow cytometer is present in an enclosure defined by the BSH and the flow cytometer instrument base" does not mean that all components of the flow cytometer are necessarily contained within the main enclosure. Instead, such a phrase means that at least the flow path (i.e., the potential aerosol generating components: the sample loading region, the particle interrogation region, and the particle collection region) of the flow cytometer is present in the main enclosure. In the depicted embodiment, a user is manipulating one of the detector arrays of the flow cytometer.

FIG. 3D depicts a flow cytometer instrument base 100 having multiple removable fluid sources in a drawer that is extendible from the base. In the depicted embodiment, a user has extended the base and has gained access to the removable fluid sources. Hoses can be seen that fluidically couple the fluid sources to other components of the flow cytometer system.

FIG. 4 depicts a cutaway schematic of one embodiment of a biosafety hood (BSH) having an aerosol management system (AMS) 240 that is fluidically coupled via conduit 220 a sample manipulation chamber 320 of the particle collection region of a flow cytometer 300. The sample manipulation chamber 320 of the particle collection region has an opening for an air filter 310 facing toward the front of the flow cytometer 300. The BSH depicted has an upper region that houses first and a second air filtration systems 250. When the AMS 240 is operating (i.e., when the AMS is actuated), air flows from the front of the flow cytometer, through a forward-facing air filter 310, through the sample manipulation chamber 320 of the particle collection region, toward the back of the flow cytometer, into the conduit 220, and toward the blower of the AMS 240.

FIG. 5 depicts cutaway schematics (zoomed in compared to FIG. 4) of one embodiment of a flow cytometer system where the sample manipulation chamber 320 of the particle collection region of a flow cytometer is fluidically coupled via conduit 220 to an aerosol management system (AMS) of a biosafety hood (BSH). The sample manipulation chamber 320 of the particle collection region has an air filter 310 facing toward the front of the flow cytometer. When the associated AMS (not depicted) is operating (i.e., when the AMS is actuated), gas (e.g., ambient air, decontamination gas, etc.), in some cases containing aerosols, flows (depicted with arrows) from the front of the flow cytometer, through a forward-facing air filter 310, through the sample manipulation chamber 320 of the particle collection region, toward the back of the flow cytometer, into the conduit 220, and toward the AMS.

FIG. 6 is a schematic representation of one example of an instrument control panel of a biosafety hood (BSH). In the depicted embodiment, the blower of the AMS can be controlled independently from the main blower (i.e., the blower of the first air filtration system) by a grouping of 3 buttons (on the left) marked "Off", "Low", and "High", which control the flow rate of the AMS blower independently from the flow rate of the main blower. The instrument panel depicted further includes a second grouping of buttons (on the right) for controlling the BSH. The left of the 3 BSH buttons controls a light of the BSH (e.g., turns it on and off). The middle of the 3 BSH buttons controls the main blower (e.g., turns it on or off). In some cases, the button on the instrument panel can control the "On" versus "Off" state while the flow rate of the main blower can be controlled elsewhere (e.g., using a different button or dial located elsewhere on the BSH; using a processor, e.g., a computer, that can control components of the flow cytometer system; etc.). The right of the 3 BSH buttons silences an alarm. For example, in some cases an alarm may sound if the sash is not closed during a flow cytometric procedure, or an alarm may sound if the flow rate of an air filtration system is above or below a threshold, etc. In some such cases, button like the one depicted allows the user to silence the alarm.

FIG. 7 depicts a schematic of one embodiment of a sample manipulation chamber. The depicted sample manipulation chamber includes: (i) an influx opening (a filter port) 350 for a filter on one side to allow clean air into the sample manipulation chamber; (ii) an efflux opening (an AMS port) 360 on one side that can fluidically couple to an AMS, e.g., the opening can be connected to a conduit (e.g., a hose, flexible tubing, flexible ducting, etc.) that can connect to an AMS (FIG. 4), which can generate air flow; (iii) an opening (a flow path port) 370 to allow the flow path of the flow cytometer to enter the sample manipulation chamber; (iv) an access port 380 for a sample manipulation arm (e.g., in this case rectangular access port); and access ports 390 for additional components (e.g., wires, cords, etc.). The sample manipulation chamber depicted also includes support feet 340.

Methods

Aspects of the present disclosure include methods of using a subject flow cytometer system. Provided are methods of performing a flow cytometric procedure. The methods generally include introducing a sample into a subject flow cytometer system (described in detail above); and flow cytometrically analyzing particles of the sample. In some cases, the methods include actuating at least one of the first (main) and second (AMS) air filtration systems of a subject flow cytometer system. For example, in performing a flow cytometric analysis, a user can actuate a first and/or second air filtration system to remove aerosols generated during the analysis (i.e., during operation of the flow cytometer).

The term "flow cytometrically analyzing" is used herein to mean the analysis of particles using a flow cytometer. As described above, analysis can include recording data associated with various measured parameters (e.g., light scatter, fluorescence, etc.) of particles in a sample. In some cases, "flow cytometrically analyzing" includes sorting particles based on the measured parameters.

A "sample" as used herein refers to any particle-containing liquid sample suitable for flow through the flow path of a flow cytometer. Dangerous aerosols can be generated during a flow ctyometric procedure even if the contained particles are not cells. For example, in some cases, a sample contains microparticles, which may be considered biohazardous under certain circumstances (e.g., if the microparticles are labeled with hazardous labels such as toxins or radioactive elements). In some cases, a sample contains viruses. Particles contained in the sample are generally separated from one another to allow for flow through the flow path of a flow cytometer.

A "biological sample" encompasses a variety of sample types obtained from an organism (or obtained in vitro, e.g., via cell culture) that is substantially in liquid form. Particles contained in the biological sample are generally separated from one another to allow for flow through the flow path of a flow cytometer. The definition encompasses blood, blood-derived samples, and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, enrichment for certain components, or labeling (e.g., labeling with a label). The term "biological sample" encompasses a clinical sample, and also includes cells in culture, cell supernatants, cell lysates, serum, plasma, cerebrospinal fluid, urine, saliva, biological fluid, and tissue samples. Any convenient method for preparing a biological sample (e.g., a biopsy) for use in a flow cytometric assay can be used.

Also provided are methods of decontaminating a flow cytometer system. Such methods are described in detail above and can include: (a) sealing the main enclosure to create a mini-environment comprising the flow cytometer; (b) introducing a decontamination gas into the mini-environment; and (c) removing the decontamination gas from the mini-environment. Decontamination can be performed manually, or various steps (or all steps) of decontamination can be performed in an automated manner (i.e., controlled by a processor). In some embodiments, the sash of a BSH is closed by the user and a decontamination button on an instrument panel of the BSH is then depressed to initiate introduction of the decontamination gas into the mini-environment. In some cases, once depressed, an automated decontamination procedure will proceed and the user can reopen the sash once the procedure is finished.

The step of sealing the main enclosure to create a mini-environment refers to a step of forming the air tight seals. For example, if rubber gaskets are used where the BSH and instrument base meet, sealing the main enclosure may encompass locking down clamps to assure a tight seal. As described above, in some embodiments, a subject BSH has a moveable panel (e.g., a sliding sash) that can be closed. In some such cases, the step of sealing the main enclosure to create a mini-environment includes closing the moveable panel in such a way that an air tight seal is formed (e.g., using locking clamps, simply sliding a sash into a locked position, using an automated locking and sealing mechanism, etc.).

Step (b), the step of introducing a decontamination gas into the mini-environment, refers to the controlled introduction of a known gas (exemplary decontamination gases are provided above) into the mini-environment. The decontamination gas is allowed to remain in the mini-environment for a period of time sufficient to provide the desired level of decontamination, and such periods of time (exposure times) will be depend on many factors including temperature, air flow, volume of the mini-environment, formulation and concentration of the gas, suspected level of contamination, etc. In some cases, the duration of at least one processor-controlled step of the decontamination procedure can be input into a processor by a user. For example, in some embodiments, the user chooses the amount of time (e.g., using an instrument panel of the BSH, using an associated processor such as a computer, etc.) that the decontamination gas will remain in the mini-environment prior to being removed (e.g., via actuation of the main blower and/or AMS blower).

In some embodiments, a decontamination procedure includes a step of modulating flow of the decontamination gas (e.g., circulating the decontamination gas) within the mini-environment, thus increasing exposure of surfaces to the decontamination gas. In some embodiments, modulating flow includes actuating an air filtration system (e.g., actuating the blower of the main air filtration system and/or the blower of the AMS). In some cases, modulating flow includes alternatively, and repeatedly actuating the blower of the main air filtration system and actuating the blower of the AMS (e.g., "pulsing" the blowers of the air filtration systems). In some embodiments, modulating flow of the decontamination gas is automated such that the user does not control the modulating step. In some embodiments, the user has the option to include or not include (e.g., turn "on" or "off" the feature) the step of modulating flow. In some cases, the user can control various parameters of the modulating step (e.g., the flow rate(s) of one or more of the air filtration systems, the timing of blower "pulses", the strength of blower "pulses", the duration of blower "pulses", etc.). In some embodiments, various alternative configurations of the above parameters are pre-programmed into a processor (e.g., a processor of the BSH, a processor of an associated computer, etc.) and a user can choose which configuration to select.

In some embodiments, the evacuation ports of the air filtration systems are closed and the decontamination gas is re-circulated during the step of modulating flow. In some cases, the evacuation ports of the air filtration systems are open during the step of modulating flow, and decontamination gas is continually added to the mini-environment, thus creating a flow of decontamination gas from the gas source to the evacuation port.

Utility

Embodiments of the subject flow cytometer systems and methods find use in a variety of different applications where it is desirable to remove aerosols from the air surrounding a flow cytometer. Embodiments of the subject flow cytometer systems and methods find use in the safe use of a flow cytometer for the analysis/evaluation of hazardous substances, including hazardous chemicals and/or hazardous particles (e.g., toxins, infectious disease agents, infected cells, etc.), which can become airborne in the form of aerosols while performing a flow cytometric procedure. The flow cytometer systems of the present disclosure provide aerosol containment for external personal protection and internal protection of the flow cytometer instrument. Airborne hazardous substances generated during flow cytometer operation are in the form of small particles. These particles are directed away from operators by an air flow system, in some cases to collection filters (e.g., High Efficiency Particulate Air (HEPA) filters). The hazardous airborne substances are also managed away from the instrument itself where they could contaminate surfaces, thereby exposing operators who may come in contact with work surfaces.

For example, a flow cytometric system of the disclosure can provide a safe system with which to perform flow cytometric analysis of clinical and/or research samples. For example, in some cases, a clinical sample (e.g., blood, serum, urine, lymph, ascites, and the like) may be contaminated with harmful organisms (e.g., bacteria, fungi, protists, etc.) and/or may contain human cells infected with virus (e.g., human immunodeficiency virus (HIV), ebola virus, hanta virus, herpes simplex virus, etc.), and the subject flow cytometric systems provide an environment for performing powerful experimental procedures (e.g., cell analysis and/or sorting) under safe conditions for the user.

Thus, the flow cytometer systems of the disclosure provide for removal of hazardous aerosols from areas of potential human exposure to a filtration system where they are removed (e.g., trapped) and rendered harmless. Further, flow cytometer systems of the disclosure provide for removal of hazardous aerosols from areas where they may collect on surfaces that would then come into human contact via operation of the instrument. Flow cytometric systems of the disclosure also provide an environment for flow cytometric analysis with a greatly reduced risk of cross-contamination of samples. For example, when particles (e.g., cells) are sorted and collected, it is important that collected samples are not contaminated with aerosols (e.g., cells) from a previous use.

In addition, footprint, overall size, cost, and complexity are kept low because a subject biosafety hood and flow cytometer are tailored to one another. The flow cytometric systems of the disclosure provide advances in the art of bio-safety protection by tightly integrating a customized hood around a customized instrument platform to achieve a high level of integration. Foot print, overall size, cost, and complexity are reduced because hood and instrument are tailored to one another. This integration of components affords several advantages: (1) a small footprint; (2) biosafety protection beyond EN12469 standards; (3) an optional redundant aerosol management system (AMS), which provides a second air filtration system (for example, while the biosafety hood protects the operator from aerosol exposure during a flow cytometric procedure, the built-in AMS also evacuates aerosols; and the AMS can operate independently of the BSH for an added measure of safety); (4) modularity (e.g., a flow cytometer system including an instrument base and a flow cytometer, to which a subject BSH may be added), which allows an upgrade in a matter of a few hours; (5) design considerations that provide a highly serviceable platform; (6) an easy-to-use decontamination procedure; and (7) an instrument base that can house flow cytometer fluidics (e.g., an easily accessible fluids and/or waste container and/or sheath and cleaning fluid tanks, which can be located in an easy to reach drawer at the base of the system).

Moreover, some embodiments provide communication between the instrument and mini-environment to monitor specific error conditions and take appropriate, safe action if triggered. This provides walk-away monitoring of the biosafety enclosure to ensure a system malfunction does not cause an exposure to hazardous aerosols. In some cases, a flow cytometer system include an instrument base and a flow cytometer (e.g., without a BSH), but the system is upgradeable (e.g., to include a BSH by attaching the BSH to the instrument base, thereby enclosing the associated flow cytometer) without loss of calibration or disruption to instrument operation.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A flow cytometer system, the system comprising:
   (a) a flow cytometer instrument base;
   (b) a flow cytometer associated with a surface of the instrument base, wherein the flow cytometer comprises:
      (i) a sample loading region,
      (ii) a particle interrogation region enclosed in a sample manipulation chamber, and
      (iii) a particle collection region; and
   (c) a biosafety hood (BSH) attached to the flow cytometer instrument base so that the flow cytometer is present in an enclosure defined by the BSH and the flow cytometer instrument base, wherein the BSH comprises a first air filtration system and an aerosol management system (AMS) comprising a second air filtration system that is fluidically coupled to the sample manipulation chamber, wherein the first and second air filtration systems each comprise an air filter and a blower.

2. The flow cytometer system according to claim 1, wherein the BSH comprises an instrument control panel configured to control a blower of the first and/or second air filtration systems.

3. The flow cytometer system according to claim 1, wherein at least one air filter of at least one of the first and second air filtration systems is a High Efficiency Particulate Air (HEPA) filter.

4. The flow cytometer system according to claim 1, wherein at least one blower of at least one of the first and second air filtration systems comprises a fan.

5. The flow cytometer system according to claim 1, wherein the first and second air filtration systems are independently operable.

6. The flow cytometer system according to claim 1, wherein the BSH further comprises a processor configured to control the first and second air filtration systems.

7. The flow cytometer system according to claim 6, wherein the processor is configured to control flow of decontamination gas from a gas source to within the enclosure defined by the BSH and the flow cytometer instrument base.

8. The flow cytometer system according to claim 1, wherein the BSH is configured to perform a decontamination procedure.

9. The flow cytometer system according to claim 8, further comprising a gas source that is in fluidic communication with the enclosure defined by the BSH and the flow cytometer instrument base.

10. The flow cytometer system according to claim 9, wherein the flow cytometer system is configured so that the first and/or second air filtration system can modulate flow of gas from the gas source into the enclosure defined by the BSH and the flow cytometer instrument base.

11. The flow cytometer system according to claim 9, wherein the flow cytometer system is configured so that the first and/or second air filtration system can modulate removal of gas from the enclosure defined by the BSH and the flow cytometer instrument base.

12. The flow cytometer system according to claim 1, wherein the sample manipulation chamber comprises a first port for air influx, a second port for air efflux, and a third port for entry of a flow path of the flow cytometer into the sample manipulation chamber.

13. The flow cytometer system according to claim 12, wherein the sample manipulation chamber further comprises a fourth port for access to samples that are within the sample manipulation chamber.

14. The flow cytometer system according to claim 13, wherein the flow cytometer system comprises a sample manipulation arm that penetrates into the sample manipulation chamber through the fourth port.

15. The flow cytometer system according to claim 14, wherein the sample manipulation arm is a robotic arm.

16. A method of performing a flow cytometric procedure, the method comprising:
   (a) introducing a sample into a flow cytometer system according to claim 1; and
   (b) flow cytometrically analyzing particles of the sample.

17. A method of decontaminating a flow cytometer system according to claim 8, the method comprising:
   (a) sealing the enclosure defined by the BSH and the flow cytometer instrument base to create a mini-environment comprising the flow cytometer;
   (b) introducing a decontamination gas into the mini-environment; and
   (c) removing the decontamination gas from the mini-environment.

18. A flow cytometer system, the system comprising:
   (a) a flow cytometer instrument base;
   (b) a flow cytometer associated with a surface of the instrument base, wherein the flow cytometer comprises:
      (i) a sample loading region,
      (ii) a particle interrogation region, and
      (iii) a particle collection region; and
   (c) a biosafety hood (BSH) attached to the flow cytometer instrument base so that the flow cytometer is present in an enclosure defined by the BSH and the flow cytometer instrument base, wherein the BSH comprises:
      (i) a first air filtration system,
      (ii) an aerosol management system (AMS) comprising a second air filtration system that is fluidically coupled to the particle collection region, wherein the first and second air filtration systems each comprise an air filter and a blower, and
      (iii) a processor configured to control the first and second air filtration systems, wherein the processor is configured to do at least one of: receive an input from the flow cytometer; and send a signal to the flow cytometer.

19. The flow cytometer system according to claim 18, wherein the processor is configured to receive an input from the flow cytometer and to send a signal to at least one of the first and second air filtration systems in response to the input.

20. The flow cytometer system according to claim 18, wherein the processor is configured to receive an input from at least one of the first and second air filtration systems, and to send a signal to the flow cytometer in response to the input.

21. The flow cytometer system according to claim 18, wherein the particle collection region is enclosed in a sample manipulation chamber that is fluidically coupled to the second air filtration system.

* * * * *